US011253797B2

(12) United States Patent
Fabis et al.

(10) Patent No.: US 11,253,797 B2
(45) Date of Patent: Feb. 22, 2022

(54) CHROMATOGRAPHIC DEVICE AND METHOD FOR ISOLATING AND PURIFYING NUCLEIC ACIDS

(71) Applicant: Qiagen GmbH, Hilden (DE)

(72) Inventors: Roland Fabis, Hilden (DE); Markus Müller, Hilden (DE); Jörg Hucklenbroich, Hilden (DE); Mario Scherer, Hilden (DE)

(73) Assignee: QIAGEN GmbH, Hilden (DE)

( * ) Notice: Subject to any disclaimer, the term of this patent is extended or adjusted under 35 U.S.C. 154(b) by 0 days.

(21) Appl. No.: 15/204,706

(22) Filed: Jul. 7, 2016

(65) Prior Publication Data

US 2016/0317949 A1 Nov. 3, 2016

Related U.S. Application Data

(62) Division of application No. 13/639,816, filed as application No. PCT/EP2011/055557 on Apr. 8, 2011, now abandoned.

(30) Foreign Application Priority Data

Apr. 8, 2010 (EP) ..................................... 10003766

(51) Int. Cl.
| | |
|---|---|
| B01D 15/34 | (2006.01) |
| B01D 15/22 | (2006.01) |
| B01J 20/291 | (2006.01) |
| B01J 20/285 | (2006.01) |
| C07H 1/08 | (2006.01) |
| C07H 21/04 | (2006.01) |

(52) U.S. Cl.
CPC ............. *B01D 15/34* (2013.01); *B01D 15/22* (2013.01); *B01J 20/285* (2013.01); *B01J 20/291* (2013.01); *C07H 1/08* (2013.01); *C07H 21/04* (2013.01)

(58) Field of Classification Search
None
See application file for complete search history.

(56) References Cited

U.S. PATENT DOCUMENTS

| | | | |
|---|---|---|---|
| 4,035,234 | A | 7/1977 | Schutt |
| 5,393,672 | A | 2/1995 | Ness et al. |
| 5,552,325 | A | 9/1996 | Nochumson et al. |
| 5,654,179 | A | 8/1997 | Lin |
| 5,817,775 | A | 10/1998 | Isaksson et al. |

(Continued)

FOREIGN PATENT DOCUMENTS

| | | |
|---|---|---|
| EP | 0 261 956 A2 | 3/1988 |
| EP | 1 245 674 A2 | 10/2002 |

(Continued)

OTHER PUBLICATIONS

GE Healthcare Media (Data file 18-1060-88 AD; 2008) (Year: 2008).*

(Continued)

*Primary Examiner* — Ryan B Huang
(74) *Attorney, Agent, or Firm* — Seed IP Law Group LLP

(57) ABSTRACT

The present invention relates to a chromatographic device for isolating and purifying nucleic acids, preferably genomic DNA, by gel filtration chromatography, a method for isolating and purifying nucleic acids, preferably genomic DNA, using this device and a kit comprising this device.

21 Claims, 14 Drawing Sheets

(56) References Cited

U.S. PATENT DOCUMENTS

| | | | |
|---|---|---|---|
| 5,877,141 | A | 3/1999 | Gabriel et al. |
| 6,410,274 | B1* | 6/2002 | Bhikhabhai .......... C12N 15/101 435/174 |
| 2002/0012990 | A1* | 1/2002 | Lander ............... C12N 15/1003 435/320.1 |
| 2002/0040873 | A1* | 4/2002 | Wahlberg ............... B01D 15/34 210/635 |
| 2003/0091989 | A1* | 5/2003 | Davis ................. C12N 15/1017 435/5 |
| 2006/0084130 | A1 | 4/2006 | Delsys et al. |
| 2006/0188892 | A1* | 8/2006 | Latham .............. C12N 15/1003 435/6.12 |
| 2008/0033160 | A1 | 2/2008 | Yang |
| 2009/0232808 | A1 | 9/2009 | Priest et al. |
| 2010/0048867 | A1* | 2/2010 | Mueller ............... C12N 15/101 530/344 |
| 2010/0331534 | A1 | 12/2010 | Khan et al. |
| 2013/0172539 | A1 | 7/2013 | Miyagi et al. |

FOREIGN PATENT DOCUMENTS

| | | |
|---|---|---|
| EP | 1 743 939 A2 | 1/2007 |
| EP | 2 270 151 A1 | 1/2011 |
| WO | 95/24498 A1 | 9/1995 |
| WO | 96/00228 A1 | 1/1996 |
| WO | 96/36706 A1 | 11/1996 |
| WO | 99/16869 A1 | 4/1999 |
| WO | 01/94574 A2 | 12/2001 |
| WO | 2006/130632 A2 | 12/2006 |
| WO | 2007/050327 A2 | 5/2007 |
| WO | 2009/127350 A1 | 10/2009 |

OTHER PUBLICATIONS

BioGenex "Safety Data Sheet—EZ Dewax Solution, Ready to Use," XP-002602420, 90 pages (Oct. 30, 2003).

Buesa, R.J. et al., "Histology without xylene," *Annals of Diagnostic Pathology* 13:246-256 (2009).

Epicentre Biotechnologies—SoilMaster™ DNA Extraction Kit, Cat. Nos. SM02050, SM02005, SC04350, and SR04350, XP002604830, Retrieved from the Internet: URL:http://www.epibio.com/pdftechlit/178pl0310, (Retrieved on Jun. 9, 2010) 4 pages (Mar. 29, 2010).

Forcic et al., "Purification of genomic DNA by short monolithic columns," *Journal of Chromatography A* 1065:115-120 (2005).

"Fungus," Wikipedia.com (accessed Jun. 3, 2013) (28 pages).

Hanselle et al., "Isolation of genomic DNA from buccal swabs for forensic analysis, using fully automated silica-membrane purification technology," *Legal Medicine* 5:S145-S149 (2003).

Helig et al., "Large-Scale Preparation of Plasmid DNA.," *Current Protocols in Molecular Biology*, Chapter 1, Units 1.7.1-1.7.16 (1998).

"How Many Species of Bacteria Are There?" wisegeek.com (accessed Sep. 23, 2011) (2 pages).

Macherey-Nagel, Viral DNA/RNA Isolation, User Manual, NucleoSpin® 8 Virus, Nucleospin® 8 Virus Core Kit, 30 pages (Mar. 2010).

"Mammal," Wikipedia.com (accessed Sep. 22, 2011) (17 pages).

"Murinae," Wikipedia.com (accessed Mar. 18, 2013) (21 pages).

Okello et al., "Comparison of methods in the recovery of nucleic acids from archival formalin-fixed paraffin-embedded autopsy tissues," *Analytical Biochemistry* 400(1):110-117 (2010).

"Plant," Wikipedia.com (accessed Mar. 8, 2013) (12 pages).

Prodělalová et al., "Isolation of genomic DNA using magnetic cobalt ferrite and silica particles," *Journal of Chromatography A* 1056:43-48, 2004.

Qiagen, QIAamp® DNA Stool Mini Kit Handbook, XP002604829, 40 pages (Aug. 2001).

Qiagen, User-Developed Protocol: Purification of viral RNA and DNA from 1000 µl of plasma, serum, and cell-free body fluids using the QIAmp® MinElute® Virus Vacuum Kit, XP002587174, 6 pages (Jun. 2004).

Sambrook et al. (eds.), Molecular Cloning: A Laboratory Manual: Third Edition—vol. 1, Cold Spring Harbor Laboratory Press, New York, "Protocol 8: Purification of Plasmid DNA by Precipitation with Polyethylene Glycol," 8 pages (2001).

USB Corp., PrepEase® Tissue & Cells DNA Spin Kit, Product Nos. 78860, 78861, 78862, Brief Protocol, XP002587173, 2 pages (2008).

"Virus," Wikipedia.com (accessed Nov. 24, 2012).

Zhou et al., "DNA Recovery from Soils of Diverse Composition," *Applied and Environmental Microbiology* 62(2):316-322 (Feb. 1996).

\* cited by examiner

6: Plastic Ring
5: Bottom Frit

CHROMATOGRAPHIC DEVICE AND METHOD FOR ISOLATING AND PURIFYING NUCLEIC ACIDS

CROSS REFERENCE TO RELATED APPLICATIONS

The present application is a divisional application of U.S. application Ser. No. 13/639,816, which is a U.S. national phase application of PCT/EP 2011/05557 filed Apr. 8, 2011, which claims priority to EP Application No. 10003766.2, filed Apr. 8, 2010. U.S. application Ser. No. 13/639,816 is herein incorporated by reference in its entity.

BACKGROUND

The isolation of high-quality nucleic acids is a prerequisite for many different techniques in modern molecular biology, such as PCR amplification, blotting analysis and genomic-library construction, used for example in the field of molecular diagnostics. Especially if the nucleic acids are obtained from biological samples containing cellular material, it is necessary to separate them from contaminants like proteins, lipids and other cellular constituents that otherwise may interfere with restriction enzymes, ligases, and/or thermostable DNA polymerases used in these downstream applications. Furthermore, RNA nucleases (RNases) and particularly DNA nucleases (DNases) present in biological samples have to be removed to prevent degradation of the DNA.

A variety of different methods have been developed for the isolation of genomic DNA from biological samples containing cellular components. All of these methods involve a step of disrupting and lysing the starting material by breaking the cellular membrane releasing its contents into solution. The solution obtained is called lysate. In the following steps proteins, in particular nucleases, and other contaminants are removed from the lysate, and finally the (more or less) purified DNA has to be recovered (an overview can be found in the QIAGEN brochure on "Genomic DNA Purification"). The step of purifying the DNA is of utmost importance, as carryover of contaminants such as salts, detergents, organic solvents, in particular phenol and ethanol, often inhibit performance of DNA in downstream applications.

A very simple and fast technique for the isolation of genomic DNA from cell lysates is to incubate the cell lysates at high temperatures, e.g., at 90° C. for about 20 min or to directly use the lysates after an additional protease digestion. However, these lysates usually contain enzyme-inhibiting contaminants such as a high salt load, and accordingly these methods, which are considered as quick and dirty techniques, are only appropriate for a limited range of applications.

So-called salting-out methods, wherein proteins and other contaminants are precipitated from the crude cell lysate by adding a solution comprising a high concentration of a salt, such as potassium acetate or ammonium acetate, are well-known techniques for separating DNA from other cellular components present in a cell lysate. The precipitates formed are then removed from the solution comprising the DNA by centrifugation, and the DNA is recovered from the supernatant by precipitation with alcohol in a further step. In these methods, removal of proteins, in particular nucleases, and other contaminants often is quite inefficient, and an additional RNase treatment, a dialysis and/or repeated precipitations by alcohol are necessary to obtain DNA sufficiently pure to be used in downstream applications, which renders the methods tedious and time-consuming.

Another possibility to separate DNA from the other compounds present in a cell lysate is to extract the contaminants from the lysates using organic solvents. In a first step, the cells typically are lysed using a detergent, and the lysates are then extracted using solvents, such as phenol, chloroform, and isoamyl alcohol, to remove the contaminants. The toxicity of the solvents used is one drawback of these methods. Furthermore, special attention has to be paid to the pH and salt concentration to ensure that the majority of contaminants are extracted into the organic phase, while the DNA remains within the aqueous phase. The DNA is then recovered from the aqueous phase by alcohol precipitation. Even though organic extraction methods are very time-consuming, the DNA isolated using these methods often contains residual phenol and/or chloroform, which act as inhibitors in downstream applications such as PCR. In addition, toxic waste is generated which has to be disposed in accordance with hazardous waste guidelines.

In recent years sorption procedures based on ion exchange, affinity and/or hydrophobic interactions have been developed in order to minimize DNA degradation during purification. In these sorption procedures, the DNA is more or less specifically "sorbed", that is either adsorbed, absorbed or chemically bound, to a stationary solid phase, comprising a resin or a matrix, due to specific interactions between the DNA and the solid phase, while contaminants do not interact with the solid phase to the same extent as DNA does, and thus may be separated from the sorbed DNA, e.g., by a washing step. Once the contaminants have been removed, the DNA has to be recovered from the solid phase by an eluting step, which usually includes a step of rinsing the solid phase with a solution (mobile phase) comprising compounds that minimize the interaction between the solid phase and the DNA, thus removing the DNA from the solid phase. The mobile phase comprising the DNA (eluate) is then collected. These solid phase-based methods enable an automation of the process of DNA isolation and purification. In addition, also rather minute amounts of DNA can be reliably processed using these methods.

Anion-exchange methods are based on the interaction between the negatively charged phosphates of the nucleic acids and positively charged surface molecules on the anion-exchange carrier (Forcic et al., *J. Chromatogr. A* 2005, 1065(1), 115-120). Under low-salt conditions DNA present in solution selectively binds to the stationary phase, and impurities such as RNA, cellular proteins, and metabolites may be washed away from the stationary phase using medium-salt buffers. In the next step, DNA can be eluted from the stationary phase using a buffer containing a high concentration of salt. The purified DNA is then recovered from the eluate by alcohol precipitation.

In silica-based methods, nucleic acids are selectively sorbed to a silica-gel membrane in the presence of high concentrations of chaotropic salts (Hanselle et al. *Leg Med* (Tokyo) 2003, 5 Supp. 1, S145-S149). RNA, cellular proteins, and metabolites are washed away from the membrane, and the DNA is then eluted from the silica-gel membrane using a low-salt buffer.

Also solid-phase methods based on the interaction between DNA and magnetic particles as a stationary phase are known in the state of the art (Prodĕlalová et al. *J. Chromatogr. A* 2004, 1056, 43-48).

Even though sorption methods allow the isolation of high-quality DNA, the number of steps to be carried out in these "bind-wash-elute" routines still is comparatively high and thus time-consuming.

For this reason a need exists for a method of isolating purified nucleic acids, preferably comprising DNA, in particular genomic DNA, from processed biological samples, such as lysates obtained from biological samples, e.g., lysed tissue and blood samples, wherein the number of steps to obtain the purified nucleic acids is reduced in comparison to the known sorption procedures, such as anion-exchange and silica-based methods, without compromising the purity of the nucleic acids obtained. Such a method should enable the user to isolate and purify the nucleic acids from contaminants, such as for example proteins, in particular nucleases, lipids, and other cellular constituents. On the other hand the method should be gentle enough to minimize chemical or enzymatic degradation of the nucleic acids and mechanical shear stress, which otherwise would fragment the large genomic DNA during the course of purification. In addition, the method should be able to accommodate a wide variety of biological samples of different origin.

A detailed analysis of the known methods for isolating and purifying nucleic acids from processed biological samples, in particular from lysates obtained from cell-containing biological samples, revealed that all these methods suffer from the fact that the nucleic acids do not remain in solution during the whole procedure of isolating and purifying. Instead, the nucleic acids either have to be precipitated or has to be bound, adsorbed or absorbed onto a solid matrix in the course of the isolation/purification procedure. In consequence, additional steps of re-dissolving the nucleic acids from a precipitate or eluting it from a solid phase are necessary, which renders all of the methods mentioned above more or less time-consuming.

SUMMARY

It was therefore an object of the present invention to provide a device and a method for isolating and purifying nucleic acids from processed biological samples, preferably from lysates obtained of cell-containing biological samples, wherein the number of steps required to isolate the nucleic acids, purified from contaminants such as proteins, in particular nucleases, and other cell components is reduced in comparison to the known methods, while still ensuring high-quality nucleic acids suitable for direct subsequent analysis by techniques such as PCR.

It has now surprisingly been found that high-quality nucleic acids, preferably comprising DNA and in particular even high-quality genomic DNA can be rapidly obtained using the device and the method of the present invention, which are described in detail below.

DESCRIPTION OF THE DRAWINGS

FIG. 1a shows the device as a side-view. FIG. 1b shows a view from the upper side.

DETAILED DESCRIPTION

Figure 1A:
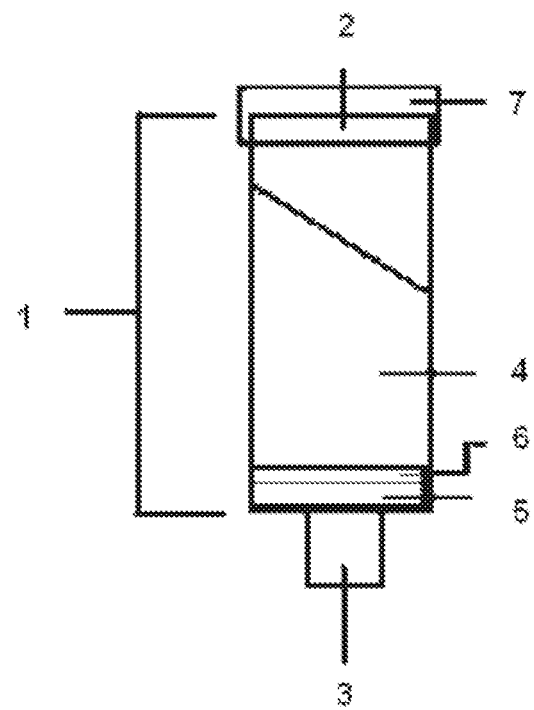
FIGS. 1a and 1b show a preferred embodiment of the chromatographic device according to the present invention.

According to the present invention the term "nucleic acids" comprise any type or DNA or RNA as well as a mixture of DNA and RNA of any type. Particularly, dependent from the conditions and the steps used, either a mixture of DNA and RNA is obtainable or highly purified DNA can be prepared, which is as well separated from RNA. If in the following the term "DNA" is used, the DNA-containing purified nucleic acid sample is meant, either comprising RNA, or separated from RNA as well. Preferably the conditions of the method are resulting in a highly purified DNA, comprising essentially no RNA.

The invention provides a chromatographic device for isolating and purifying nucleic acids, preferably comprising DNA and in particular genomic DNA, from contaminants by gel filtration chromatography, comprising at least one chromatographic unit, comprising: 1. A hollow body (1) having an inlet (2) and an outlet (3), the hollow body comprising a solid matrix providing size exclusion properties (4), preferably forming a gel bed; 2. a porous frit, filter, fleece or membrane (5), placed between the outlet (3) and the solid matrix (4) to retain the solid matrix (4) within the chromatographic unit, 3. preferably a non-porous ring (6) placed between the porous frit, filter, fleece or membrane (5) and the matrix (4), sealing the outer area of the frit, filter, fleece or membrane (5), to prevent the mobile phase from entering the frit, filter, fleece or membrane (5) without passing the matrix (4), 4. optionally at least one removable closing device (7) to seal the inlet (2) and/or outlet (3) of the chromatographic unit, and 5. optionally at least one collection tube to collect the mobile phase (eluate) after having passed the matrix (4), wherein the solid matrix (4) preferably is a gel forming polymer having a size exclusion limit of 150 to 500 base pairs (bp), preferably 200 to 400 bp, and most preferably 250 to 300 bp. Preferably the gel forming polymer has a corresponding size exclusion limit of 10 to 10000 KDa, more preferred of 20 to 8000 kDa.

Using this device, a "negative" chromatography is possible, where in contrast to the other chromatographic methods commonly used for the chromatographic purification of DNA, not DNA, but the contaminants are sorbed to the solid matrix, thus allowing the chromatographic purification to be carried out in one single rinsing step. Accordingly, the method may be referred to as a "single-step" chromatography method. It has been surprisingly found, that the chromatographic devices of the present invention are able not only to remove contaminants of small molecular weight, but also act as a depth filter for solid material which does not enter the gel bed, but remains on its upper surface. This is even more surprising, since solid material usually tends to clock the pores of a gel, thus hampering or disturbing further chromatography.

Accordingly, the device of the present invention is in particular suitable for removing solid contaminants from a sample, especially for removing precipitates from lysates, such as for example the precipitate formed from dodecyl sulfate ions and monovalent alkali metal ions or divalent alkaline earth metal ions when the methods for lysing cells and removing dodecyl sulfates ions described in copending applications with the title "method for isolating and purifying nucleic acids" of the same applicant having the same filing date as the present application and with the title "method for precipitating anionic surfactant ions in the presence of nucleic acids" of the same applicant having the same filing date as the present application, respectively, are used. Using the chromatographic device of the present invention, an eluate containing highly purified de-salted nucleic acids, preferably DNA, in particular gDNA, essentially free from residual dodecylsulfate ions is obtained.

The chromatographic device is not limited to a special shape. Any device commonly used in chromatography may be used. The chromatographic device may be selected from, but is not limited to, a traditional column used for suction or pressure column chromatography, a spin column, or a multiwell plate. In general, so-called chromatographic columns, having a circular cross-section, are used, whose diameter is small in comparison to their length. The column may for example be of cylindrical or conical shape or a combination thereof.

Figure 1B:
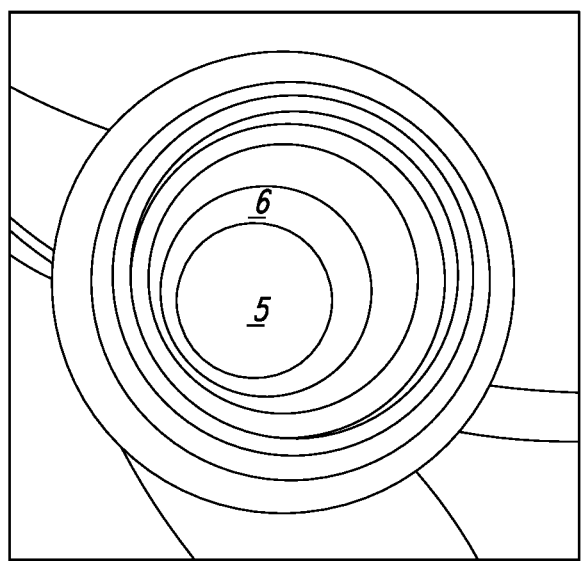

A preferred embodiment of the chromatographic device in depicted in FIG. 1, showing a hollow body (1), having an inlet (2) and an outlet (3), comprising a solid matrix (4), equipped with a porous frit (5) and a non-porous ring (6) placed between the solid matrix (4) and the porous frit (5). The inlet (2) of the chromatographic device preferably is closed with a removable screw cap (7). Note, that the upper surface of the matrix in this embodiment is not parallel to the frit due to the process of pre-spinning the column in a fixed-angle rotor.

The chromatographic device of the present invention preferably can be used for size exclusion chromatography (SEC). If an organic solvent is used as the eluent (mobile phase) SEC is also called gel permeation chromatography (GPC). In the present invention, preferably a water-based mobile phase, such as water, an aqueous organic solvent or an aqueous buffer/solution, is used as mobile phase. In this case SEC is also referred to as gel filtration chromatography. Size exclusion chromatography is a chromatographic method, wherein molecules are separated based on their size, or more precisely based on their hydrodynamic volume. Commonly, a solid matrix able to form a gel bed, when suspended in an aqueous medium, such as a dextran, agarose, polyacrylamide, or a mixture thereof, is suspended in a buffer and packed in the hollow body of a column made of glass, plastic, Teflon or any other material that neither reacts with the mobile phase nor the analyte. The sample to be purified is then applied to the center of the gel bed's upper surface, and allowed to pass through the gel, either by gravity or forced by centrifugation, or pressure. According to the present invention preferably centrifugal forces are applied to move the mobile phase down the column, wherein the columns are spun in a centrifuge (so-called spin column technique). Due to the cross-linking in the gel, pores of a certain size exist inside the gel. Small molecules are able to penetrate the pores, and therefore move through the gel bed more slowly, being retained as they pass down the column, while large molecules cannot penetrate the pores and move down the column more quickly. After having passed the column, the mobile phase (now referred to as eluate), containing the purified analyte, is then collected at the outlet of the column. To retain the solid matrix within the hollow body of the column, a porous fit, filter, fleece or membrane is preferably placed between the outlet of the column and the solid matrix. Said porous filter, frit, fleece or membrane preferably allows the passage of any nucleic acid independent from their size, up to and in particular genomic DNA.

In SEC, the size exclusion limit defines the molecular weight, above which molecules are too large to be trapped in the stationary phase. The size exclusion limit of a solid matrix can be adjusted by the degree of cross-linking in the gel. A wide variety of solid matrices able to form a gel bed with different degrees of cross-linking are commercially available. The size exclusion on the other hand preferably is not limited by the frit, filter, fleece or membrane of the chromatographic device.

A problem often encountered in gel filtration chromatography, and particular in gel filtration chromatography using spin columns, is that the mobile phase may run down along the inner wall of the column, thus entering the frit, filter, fleece or membrane without having passed the solid matrix. This is especially true for high-throughput applications, when not all of the sample solution to be purified is applied exactly to the center of the gel bed's flat surface, or the sample is applied to quickly. When the mobile phase does not enter the gel bed, no chromatographic separation occurs, and a contaminated eluate is obtained. To overcome this problem, the chromatographic device of the present invention is preferably equipped with a non-porous ring placed between the porous frit, filter, fleece or membrane and the matrix. This ring seals the outer area of the frit, filter, fleece or membrane, thus preventing the mobile phase from entering the frit, filter, fleece or membrane without having passed the matrix. In addition, the velocity of the mobile phase inside the column is slowed down, thus improving selectivity.

The non-porous ring is preferably made of a flexible or elastic material which facilitates its incorporation into the hollow body. However, a non-flexible or non-elastic material may also be used. In a preferred embodiment the non-porous ring is made based on a polyolefin or a mixture of two or more polyolefins, optionally with one or more further additives. Preferably the material forming the ring contains polyethylene or polypropylene or mixtures thereof, most preferred high density polyethylene. In a specifically preferred embodiment the part of the ring that gets into contact with the inner wall of the hollow body has at least one cut-out or recess, for example in the form of a slot, along the complete length of the outer ring or at least along a part of said length. Suitable non-porous rings are commercially available, like MG 9641 based on high density polyethylene from Borealis AG.

Optionally the chromatographic device of the present invention may contain at least one removable closing device to seal the inlet and/or the outlet of the chromatographic unit. If both the inlet and the outlet are equipped with such a removable closing device, the closing devices used to seal the inlet and those used to seal the outlet may be the same or different.

The chromatographic device of the present invention may furthermore be combined with at least one collection tube to collect the mobile phase (eluate) after having passed the matrix. According to the present invention the chromatographic device may be equipped with one collection tube per chromatographic unit, i.e., if the chromatographic device only contains one chromatographic unit, preferably only one collection tube will be used. If on the other hand the chromatographic device contains several chromatographic units for example 24, 48 or 96 chromatographic units in form of a multiwell plate, then also more than one collection tube will be used, preferably in form of a multiwell plate, too. Additional collecting tubes may be supplied for collecting the liquid drained from the column during pre-spinning.

In a preferred embodiment the gel-forming polymer is selected from the group of comprising dextrans, agarose, polyacrylamide, or mixtures thereof, and more preferably is a mixture of a dextran and a polyacrylamide. Such gel-forming polymers of different size exclusion limits are commercially available, for example under the trademark name of SEPHACRYL®, SEPHADEX®, or SEPHAROSE®. A particular preferred solid matrix is the S-400 HR SEPHACRYL® resin, commercially available from GE-Healthcare, which is a spherical allyldextran/N,N'-methylene bisacrylamide matrix with a size exclusion limit of 271 bp (corresponding to 20-8000 kDa). Further suitable gel-forming polymers may have a methacrylic basis, like a hydroxylated methacrylic polymer, for example, TOYOPEARL® HW 65 available from Tosoh Bioscience LLP (former TosoHaas) with a size exclusion limit of 40 to 5000 kDa.

In a preferred embodiment of the present invention, the removable closing device preferably is a disposable closing device, selected from the group comprising, preferably consisting of lit foils, seals and break-away ends, or a re-closable closing device, selected from the group comprising, preferably consisting of screw caps and snap-on caps. In a further preferred embodiment, both the inlet and the outlet of the chromatographic unit are sealed with the removable closing device, and the solid matrix is supplied in the form of a gel, preswollen in a solvent selected from the group comprising water, the homogenous mixtures of organic solvents with water, or aqueous buffers. In this embodiment, the solvent is preferably purged from the chromatographic unit, while simultaneously establishing the matrix in form of a matrix bed by centrifugation immediately prior to use (pre-spinning).

A further embodiment of the present invention is a chromatographic device comprising a plurality of chromatographic units in a parallel fashion, preferably in the form of a multiwell plate wherein each well of the multiwell plate contains one separate chromatographic unit.

The invention further provides a method for purifying nucleic acids, preferably DNA, in particular genomic DNA, by gel filtration chromatography using a chromatographic device according to the present invention, comprising the steps of: 1. Providing a sample comprising the nucleic acids to be purified, preferably having at least 400 bp, preferably 500 bp, more preferred at least 600 bp, wherein the sample is in the form of the solution or a suspension in a liquid eluent, preferably an aqueous eluent, 2. establishing a matrix, preferably a matrix bed in the chromatographic unit preferably by centrifugation (pre-spinning), 3. applying the sample to (the center of) the matrix (bed) upper surface, 4. eluting the nucleic acids from the chromatographic unit by centrifugation and simultaneously collecting the eluate. In a particularly preferred embodiment no further step is comprised between step 3 and step 4. This means step 3 is immediately followed by step 4.

The sample to be purified preferably is a processed biological sample, more preferably a lysate obtained from any biological sample. Said biological sample preferably is a cell-containing biological sample, more preferably selected from the group of fresh and frozen tissue, blood or other body liquids and Gram-negative bacteria.

Using the method of the present invention, in principle all kind of nucleic acids like deoxyribonucleic acid (DNA) and/or ribonucleic acid (RNA) can be isolated from a wide variety of processed biological samples, including synthetic, genetically engineered or naturally occurring single-stranded or double-stranded DNA, oligo- and polynucleotides of deoxyribonucleotides or ribonucleotides, fragments of DNA obtained by partly digesting DNA using restriction endonucleases, mitochondrial DNA, plasmid DNA, and metagenomic DNA, representing the entirety of DNA obtained from all microorganisms found in a biotope or a biocenosis. Preferably the method of the present invention is used for isolating and purifying genomic DNA, which in terms of the present invention is the high molecular weight DNA obtained from one single organism, comprising the entirety of genetic information of this organism, in contrast to plasmid DNA, DNA partly digested by the action of restriction endonucleases, and metagenomic DNA. In this preferred embodiment, purified high molecular weight DNA is obtained, while smaller fragments of DNA are retained within the chromatographic material. Due to its high molecular weight and large size, intact high quality genomic DNA is difficult to isolate and purify, as a comparably high risk of degradation of genomic DNA exists, either by mechanical stress during the isolating procedure, in particular sheer stress, or by chemical and enzymatic degradation. Degraded DNA, on the other hand, may lead to both quantitative and qualitative errors in downstream analyses. The method of the present invention provides a fast, robust, safe, easy-to-handle and yet mild method for isolating and purifying nucleic acids, in particular genomic DNA, from a variety of different processed biological samples.

Using the method of the present invention, nucleic acids, preferably DNA and more preferred genomic DNA, can be isolated from a wide variety of processed starting materials, including, but not limited to, animal and human tissue, for example liver, spleen, lung, heart, brain, kidney, etc., animal and human blood, liquor, sputum, sperm, cell cultures of animal and human cells, animal and human bone marrow, yeast, bacteria, insects, plants, and rodent tails. Preferably, the sample is a processed cell-containing biological sample of animal or human origin. In another preferred embodiment, the samples comprise processed Gram-negative bacteria. The sample may have been lysed immediately after being taken from its natural environment (fresh sample), or may have been stabilized prior to lysis by freezing or by the action of chemical stabilizing agents, such as for example formalin-fixing and paraffin-embedding (FFPE tissue) or blood stabilizing agents comprising citrate, a cationic surfactant, like, e.g., PAXgene™ (PreAnalytiX, Germany), or Heparin. Even more preferably the sample is selected from the group comprising lysed fresh or frozen tissue and blood, most preferably from lysed mammalian tissue and blood.

The step of pre-spinning preferably is carried out by centrifuging the device at 500 to 900×g for 1 to 7 min, preferably at 700×g for 2 to 5 min, and most preferably at 700×g for 3 min.

In such an embodiment, where the matrix is provided as a matrix bed the volume of the matrix bed in the chromatographic unit preferably is in the range of 100 µL to 2 mL, more preferably in the range of 500 µL to 1 mL, and most preferably is 600 µL to 800 µl, wherein 800 µl might be particularly preferred for genomic DNA. The matrix is preferably provided as a dispersion of the gel-forming polymer in water, a salt solution, e.g., 0.9% NaCl, or a suitable buffer, like, e.g., TE, TAE, PBS or similar or in diluted buffers, whereas said dispersion comprises preferably 60-90%, more preferably 70-80% and in particular 75% of the gel-forming polymer. The filling level of the matrix bed in the chromatographic unit preferably is in the range of 0.5 cm to 2.0 cm, more preferably 1.0 to 1.5 cm. In a standard 96-well plate the volume of the matrix bed preferably is about 0.8 mL. The exact volume and the filling level of matrix bed used depend on the size and shape of the hollow body defined by the column, as well as on the kind and amount of the sample to be purified, which is well known to a person skilled in the art.

The matrix might be washed before the sample is applied to its surface. A washing step may be carried out by applying water, buffer or a salt solution, e.g., 0.5-1%, preferably 0.9% NaCl in water to the surface of the matrix and centrifuging the chromatographic device. Preferably the matrix is washed once or twice with the same amount of water, buffer or salt solution as was used for preparation, i.e., 100 µl to 2 ml, preferably 500 µl to 1 ml, more preferred 600 µl to 800 µl.

The amount of the sample applied to the matrix depends from the volume used for the matrix. Preferably a sample volume of up to about 100 µL is applied to a column packed with 600 µL to 800 µl or a filling level of 1.0 cm to 1.5 cm of matrix bed. A skilled person is able to determine the suitable sample volumes accordingly for other matrix embodiments.

The step of eluting the nucleic acids from the chromatographic unit preferably is carried out by centrifuging the device at 500 to 900×g for 1 to 7 min, preferably at 700×g for 2 to 5 min, and most preferably at 700×g for 3 min.

Using the device and the method of the present invention highly purified nucleic acids, e.g., highly purified DNA can be obtained from processed biological samples, for example from lysed tissue samples in about only 6 min (3 min pre-spinning of the column and 3 min for the chromatographic separation itself), while approximately 18 min are necessary for the purification of the same amount of lysed tissue using, e.g., the QIAamp kit (QIAGEN, Hilden, Germany).

The quality and purity of the nucleic acids isolated by the device and method of the present invention is equal, or in many cases even superior, to the quality and purity of nucleic acids obtained by state of the art methods for bench-scale purification, such as for example the very successful QIAamp technology (QIAGEN, Hilden, Germany) with respect to purity and yield as judged by UV/Vis spectroscopy, gel electrophoresis, conductivity measurements, HPLC analysis, PCR and further assays. In addition, the nucleic acids-containing eluate obtained by the method of the present invention may be frozen for longtime storage or may be processed in downstream application like quantitative real time PCR (qRT-PCR), PCR and the like, immediately after chromatography without the need for any additional steps to isolate the nucleic acids from the eluate. As the nucleic acids remain essentially in solution during the purification process, and neither is precipitated by the addition of organic solvents such as for example ethanol, nor is sorbed or bound to a solid matrix such as a silica-membrane or an anion exchange resin, the method of the present invention is much faster than the methods for isolating and purifying nucleic acids known from the state of the art. Furthermore, the method of the present invention can be fully automated.

The sample to be purified using the device and the method of the present invention preferably is a lysate. The sample preferably is a lysate obtained from a cell-containing biological sample by a preceding lysis procedure, comprising the steps of: 1. Mixing the cell-containing sample with a lysis buffer, 2. incubating the mixture to obtain a lysate comprising at least DNA, RNA and proteins, 3. optionally disintegrating the RNA present in the lysate, 4. optionally selectively precipitating dissolved contaminants from the lysate, preferably wherein the nucleic acids, particularly the DNA stays essentially in solution during all of steps 2 to 4.

For a fast, yet mild lysis of biological samples, preferably the lysis buffer described in copending application with the title "method for isolating and purifying nucleic acids" of the same applicant having the same filing date as the present application is used, which comprises a source of anionic surfactant ions, preferably sulfate ions, more preferably dodecyl sulfate ions (DS$^-$), but is essentially free of a complexing or chelating agent like, e.g., ethylenediamine tetraacetic acid (EDTA). Non-limiting examples for such agents are EDTA, EGTA, EDDS (ethylene diamine diacetic acid), NTA (nitrilo triacetic acid), gluconic acid, isoascorbic acid, tartaric acid, citric acid, iminodisuccinate, triethanolamine. Preferably this lysis buffer comprises a buffering agent, $H_2SO_4$ and a source of surfactant ions, but is essentially free of a complexing or chelating agent and $Mg^{2+}$-ions, which means that it contains less than 10 mg/L of a chelating agent and $Mg^{2+}$-ions, preferably less than 1 mg/L, more preferably less than 0.1 mg/L, even more preferably less than 0.001 mg/L, and most preferably the lysis buffer does not contain any chelating or complexing agent and $Mg^{2+}$-ions at all (0 mg/L). The lysis buffer has a pH of 7.5 to 10, preferably of 8 to 9 and most preferably of 8.5 and may additionally comprises a protease such as QIAGEN Proteinase K or QIAGEN Protease, (QIAGEN, Hilden, Germany). Anionic surfactants are, e.g., sulphates, sulfonates and carboxylates, preferably alkyl sulphates (fatty alcohol sulfates), alkane sulfonates, alkylbenzene sulfonates and alkyl carboxylates. Particularly preferred are surfactants providing surfactant ions showing similar precipitation behavior as dodecyl sulfate ions (DS$^-$), more preferred are surfactants providing sulphate ions and most preferred are surfactants providing a source of dodecyl sulphate ions. As a source of dodecyl sulphate ions any compound releasing into solution dodecyl sulphate ions ($H_3C(CH_2)_{11}SO_4^-$) upon dissolution in water may be used. The source of dodecyl sulphate ions preferably is selected from the group comprising sodium dodecyl sulphate (SDS), ammonium dodecyl sulphate and lithium dodecyl sulphate, and most preferably is sodium dodecyl sulphate. The concentration of the source of surfactant ions in the buffer depends on the sample to be lysed, but preferably is 1 to 100 mmol/L, more preferably 5 to 75 mmol/L, even more preferably 10 to 50 mmol/L and most preferably is 25 mmol/L. The buffering substance can be any suitable buffering substance providing a pH of at least 7.5 like, e.g., TRIS, HEPES, HPPS or any ammonia buffer. The preferred buffering substance is TRIS. The concentration of the buffering substance in the buffer preferably is in the range of 1 to 100 mmol/L, more preferably 5 to 75 mmol/L, even more preferably 10 to 50 mmol/L and most preferably 25 mmol/L. The molecular ratio of the buffering substance to the source of surfactant ions in the buffer preferably is in the range of 3:1 to 1:3, more preferably 2:1 to 1:2, even more preferably 1.2:1 to 1:1.2 and most preferably is 1:1. The lysis buffer may comprise further active components selected from the group comprising stabilizers such as sodium azide, solubilizing agents or the like. The concentration of chloride ions in the buffer preferably is less than 10 mmol/L, more preferably less than 1 mmol/L, even more preferably less than 0.1 mmol/L.

This buffer allows a fast lysis of sample material under low-salt lysis conditions, i.e., hypotonic conditions, which means that the total ion concentration in the buffer solution is lower than the total ion concentration within the cells to be lysed. In the case of NaCl, for example, an aqueous solution comprising less than 0.9 wt % NaCl (about 155 mmol NaCl, corresponding to about 310 µmol/L of dissolved ions) is hypotonic. Using this buffer even samples containing a rather high amount of solid material, for example tissue samples, are usually completely lysed within less than 40 min at, e.g., 56° C. Lysis may be carried out at temperatures ranging from 45° C. to 70° C., preferably from 50° C. to 68° C., and most preferred at 62° C. Preferably a buffer volume of 80 to 150 µL, more preferably of 80 to 120 µL, even more preferably of 80 to 100 µL and most preferably of 80 µL is used for the lysis of 10 mg of sample tissue. The ratio (buffer:sample) can be calculated for higher or lower amounts of sample accordingly.

RNA present in the lysate may be optionally disintegrated after lysing the sample. The step of disintegrating RNA comprises any method of reducing the amount of dissolved RNA in the lysate and/or inactivating the RNA and/or facilitating its separation from the DNA, including any method of thermally, chemically and/or enzymatically hydrolyzing, digesting, transforming and/or decomposing RNA, either partially or completely, and/or removing the RNA or its fragments from the solution, e.g., by precipitation, sorption procedures or the like. A simple method for disintegrating the RNA in the sample is by heating the sample to a temperature of at least 60° C. without any further addition of a disintegrating agent. If the RNA shall remain in the sample heating of the sample only up to 58° C., preferably up to 56° C. is recommended. In a preferred embodiment disintegrating of RNA is carried out as described in copending application with the title "method for isolating and purifying nucleic acids" of the same applicant having the same filing date as the present application, wherein the step of incubating the mixture of the biological sample and the lysis buffer, and the optional step of disintegrating the RNA present in the lysate are carried out in a single step, preferably by heating the mixture to a temperature equal to or above 60° C., preferably to 60° C. to 70° C., more preferably to 61° C. to 65° C., and most preferably to 62° C. Preferably the mixture is heated for 10 to 80 minutes (min), more preferably for 15 to 60 min, even more preferably for 20 to 50 min, and most preferably for 30 to 45 min.

Increasing the temperature during or after the lysis step up to 80° C. additionally denatures the proteins (e.g., enzymes) in the sample without affecting the desired DNA, in particular genomic DNA. In this case of course RNA is not obtained.

The amount of DNA obtained from 10 mg of a sample using the method of the present invention depends upon the sample, for example its kind and age. Usually around 5 to 70 µg genomic DNA typically is obtained from 10 mg of different tissue samples.

Amounts of about 10 mg are the amount of sample commonly analyzed in molecular diagnostics. It should, however, be understood, that using the method of the present invention, it is also possible to process larger or smaller amounts of sample material, e.g., in the g-range or µg- to ng-range, respectively. In this case, the amounts of reagents, buffers, solid matrix as well as the dimension of the chromatographic device have to be adjusted by up- or down-scaling, which is well known to a person skilled in the art.

After lysing the sample and optionally disintegrating the RNA present in the lysate as described above, surfactant ions are removed from the lysate, preferably by precipitation. Precipitating preferably is carried out as described in copending application with the title "method for precipitating anionic surfactant ions in the presence of nucleic acids" of the same applicant having the same filing date as the present application by adding to the lysate a solution (precipitating solution), comprising monovalent ions of alkali metals and/or divalent ions of alkaline earth metals selected from the group comprising, preferably consisting of $Rb^+$, $Cs^+$, $Ca^{2+}$, $Sr^{2+}$, $Ba^{2+}$, or a mixture thereof, which form an insoluble precipitate with the surfactant ions, particularly with dodecyl sulphate ions. The precipitating solution preferably comprises $Sr^{2+}$-ions. The precipitating solution comprises a water-soluble salt of alkali metals and/or alkaline earth metals, like for example $RbCl$, $SrCl_2$, $CaCl_2$ or $BaCl_2$ which upon dissolution in water provide monovalent ions of alkali metals and/or divalent ions of alkaline earth metals. The concentration of the monovalent and divalent metal ions in the precipitating solution preferable is in the range of 0.1 to 10 mol/L, preferably of 0.5 to 5 mol/L, more preferably of 0.75 to 2.5 mol/L, and most preferably of 0.9 to 1.2 mol/L. The volume of precipitating solution added to a certain volume of a liquid sample (lysate) depends upon the concentration of surfactant ions in the sample solution. In a preferred embodiment, the volume ratio of the liquid sample to precipitating solution is in the range of 4:1 to 12:1, preferably 5:1 to 11:1, more preferably 6:1 to 10:1 and most preferably 7:1 to 9:1. If for example 80 µL of a liquid sample are obtained by lysing a sample as described above, then preferably 10 µL of a 1 M precipitating solution is added to precipitate the surfactant ions.

The term precipitating is understood as a step of adding to a solution, comprising dissolved nucleic acids and surfactant ions, a substance or a mixture of substances that react with the surfactant ions to form a compound being insoluble in the resulting solution, thus precipitating from the solution. Optionally, the mixture may be incubated to ensure completeness of precipitate formation preferably at −10° C. to 10° C., preferably at −5° C. to 5° C., more preferably at −2.5° C. to 2.5° C. and most preferably at −1° C. to 1° C., preferably for 3 to 60 min, more preferably for 5 to 30 min and most preferably for about 10 min, e.g., by leaving the mixture to stand in an ice bath.

The invention further provides a kit for the isolation and purification of nucleic acids, preferably comprising DNA, in particular genomic DNA, comprising: 1. a chromatographic device according to the present invention, and one or more components selected from the group of 2. a lysis buffer, 3. a source of monovalent ions of alkali earth metals and/or divalent ions of alkaline earth metals, and optionally one or more primers for the direct amplification of one or more target nucleic acids from the eluate. Preferably the kit comprises the lysis buffer described above. In a particular preferred embodiment the kit further comprises a source of monovalent ions of alkali metal and/or divalent ions of alkaline earth metal selected from the group comprising, preferably consisting of $Rb^+$, $Cs^{2+}$, $Ca^{2+}$, $Sr^{2+}$, $Ba^{2+}$ or mixtures thereof, either in the form of water-soluble alkaline earth metal salts to be dissolved by the user, or as a stock solution to be diluted by the user, or as a ready to use solution. Further the kit preferably comprises instructions for the present isolation and/or purification method.

EXAMPLES

Materials and General Experimental Procedures

Gel filtration media were obtained from GE-Healthcare (Freiburg, Germany), ion-exchange media were obtained from Merck KgaA (Darmstadt, Germany).

Unless otherwise noted, the tissue samples analyzed were rat liver tissue samples.

Determination of the amount and purity of gDNA: To estimate the amount of gDNA (gDNA yield) in a purified sample (eluate), the absorbance of the sample was measured at a wavelength of 260 nm by UV/Vis spectroscopy. A background absorption value, measured at 320 nm was subtracted from the $OD_{260}$ value (optical density at 260 nm), and the value was multiplied by 50, the specific absorbance factor of DNA, and by the dilution factor to obtain the gDNA concentration in µg/µL. In addition, UV/Vis spectroscopy was also used to judge the purity of the DNA obtained. Residual solid particles do not exhibit a distinct absorbance peak, but lead to an elevated baseline in the whole spectrum. Free haemoglobin has an absorbance maximum at a wavelength of 410 nm, while salts and preservatives like sodium azide absorb at a wavelength below 230 nm. A Spectramax II (Molecular Devices, Sunnyvale, Calif., USA) 96-well plate photometer was used to record the UV/Vis spectra.

A more precise determination of the amount of gDNA obtained was carried out using HPLC analysis. The area under curve (AUC) for the gDNA-containing peaks in the spectra was calculated by the software and compared to a HPLC standard curve, to determine the amount of gDNA in a sample. HPLC analysis was also used to determine the purity of the samples using a Vision BioCad workstation (Perseptive Biosystems, Framingham, Mass., USA). A 0.83 mL Peek column filled with the ion exchange resin TMAE-Fractogel(S) (E. Merck, Darmstadt, Germany) was used. The samples were analyzed at a flow rate of 1.5 mL/min in an increasing $CaCl_2$ gradient, starting from 0 mmol/L to 300 mmol/L over a period of 35 column volumes, buffered at pH 7.2. The absorbance was continuously monitored at 260 nm and 410 nm.

Agarose gel electrophoresis was carried out using a 50 mL 0.8% agarose gel, containing 2.5 µL SYBR-Green II. Samples were run using a voltage of 100 Volt for a time period of 40 min. The gels were analyzed using commercially available equipment from BioRad or LTF-Labortechnik (Wasserburg, Germany).

SDS quantification: The residual SDS concentration was determined by UV/Vis spectroscopy according to a modified procedure of Rusconi et al. adapted to be used within a 96 well photometer (Rusconi et al. *Anal. Biochem.*, 2001, 295(1), 31-37). The assay is based on a specific reaction of the carbocyanine dye "Stains All" (4,5,4',5'-Dibenzo-3,3'-diethyl-9-methylthiocarbocyanine bromide) with SDS, which leads to the formation of a yellow color (absorbance maximum at 438 nm). As SDS was used as the source of dodecyl sulfate ions in the present examples, it should be understood that the amount of SDS in a solution equals the amount of dodecyl sulfate ions present in solution.

1 mL of a stock solution of the dye (1.0 mg "Stains All" in 1.0 mL 50% isopropanol) was diluted with 1.0 mL formamide and 18 mL water to obtain a ready-to-use solution of the dye. To determine the amount of SDS in a sample, 5 µL of the sample solution were placed into a microtiter plate, mixed with 100 µL of the ready-to-use solution, and incubated at room temperature for 5 min in the dark before reading the plate at 438 nm. The amount of SDS in the sample was retrieved by comparison with a calibration curve, established by recording the absorbance of solutions containing a SDS concentration of 250, 167, 111, 74, 49, 32 and 21 µmol/L, respectively, at 438 nm.

Conductivity measurement: To determine the ion strength in the samples, conductivity measurements were carried out using a Consort C831 Conductometer (LTF-Labortechnik, Wasserburg, Germany), calibrated to 20° C. A minimum volume of 2 mL is necessary for the measurement, therefore aliquots of 20 µL of each sample were diluted with 1980 µL water prior to the measurement.

PCR amplifications: Real time-PCR (qRT-PCR) assays were performed on a Rotor-Gene 2000 or 3000 cycler (Corbett, Sydney, Australia) on a 50 µL scale, or in a TaqMan 7700 analyzer (Applied Biosystems, Foster City, Calif., USA).

For the jun RT-PCR assay, a commercially available kit (Part. No: 4327113F), based on a primer/probe system (FAM) from Applied Biosystems (Darmstadt, Germany), including a 20× Jun PCR primer/probe mix was used in combination with a 2× TaqMan PCR universal master mix from Applied Biosystems.

A genomic DNA standard was purified from rat tail using the QIA-symphony platform (QIAGEN, Hilden, Germany), and was further purified by subsequent anion exchange chromatography (AEX) using a QIAGEN tip 2500 according to the manufacturers' protocol (QIAGEN, Hilden, Germany). The gDNA was stored in aliquots at −20° C. and thawed immediately prior to use.

Example 1

Removal of Precipitates Formed From Dodecyl Sulfate Ions and Strontium Ions

Co-pending applications with the title "method for isolating and purifying nucleic acids" of the same applicant having the same filing date as the present application and with the title "method for precipitating anionic surfactant ions in the presence of nucleic acids" of the same applicant having the same filing date as the present application describe a new lysis buffer comprising a source of surfactant ions and a method for selectively precipitating surfactant ions from a solution comprising such ions like dodecyl sulphate ions and DNA by adding for example strontium ions. To optimize the removal of these precipitates from the lysates different amounts of a 0.5 M aqueous solution of $SrCl_2$ (25 µL and 50 µL, respectively) were added to lysates, obtained from lysis of 10 mg of tissue by incubating the samples for 40 min at 62° C. in a lysis buffer containing TRIS and SDS, both at a concentration of 25 mmol/L, adjusted to pH 8.5 by the addition of $H_2SO_4$. After adding the precipitating solution, the mixtures were incubated at room temperature or in an ice bath (ca. 0° C.) for 10 min. The precipitates formed were then removed by centrifugation or by filtration on a short gel filtration column filled with 600 µL of GE-Healthcare S1000 SF matrix (GE-Healthcare, Freiburg, Germany), respectively.

Figure 2:
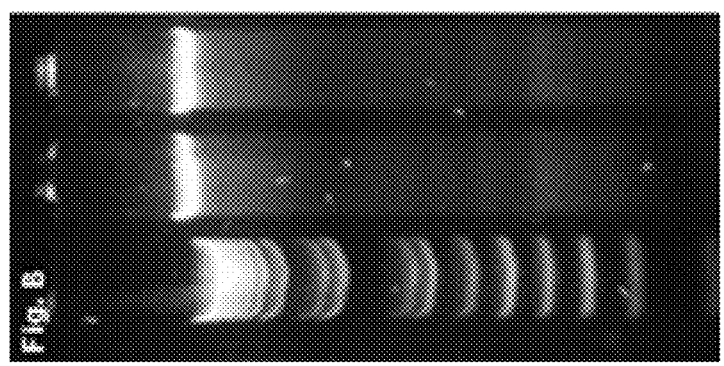
FIG. 2 shows the residual amount of SDS present in solution after using different procedures for removing the precipitate formed from divalent metal ions of alkaline earth metals and dodecyl sulfate ions (see Example 1). While no advantage of using a large of excess of precipitating solution can be detected (50 µL versus 25 µL), a filtration step (filt) is always clearly more effective in removing the precipitate than centrifugation (centrif). The best results are obtained, if the samples are incubated for 10 min in an ice bath (Ice), and then filtered.
Figure 2:
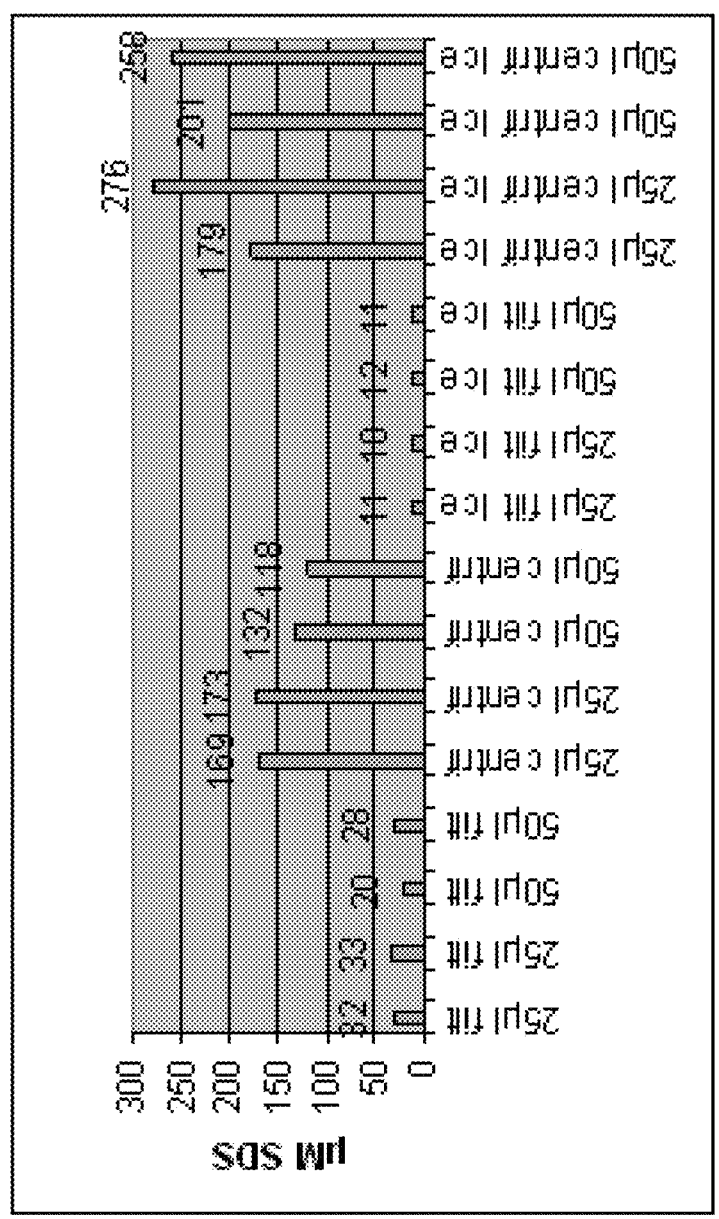

Results are presented in FIG. 2A (left hand side) and 2B (right hand side): FIG. 2A shows the residual amount of SDS [µmol/L] present in the supernatant/eluate after centrifugation (centrif) and gel filtration chromatography (filt), respectively. It can be seen that gel filtration chromatography is much more effective in removing SDS from the solution than centrifugation. The lowest amount of residual SDS in the eluate was found, when the sample was incubated in an ice bath. In this case, no advantage was observed when doubling the amount of precipitating solution added to the lysate with respect to the amount of residual SDS detected in the eluate after purification. As can be seen from FIG. 2B, strontium chloride is also effective in precipitating residual proteins. To ensure a low sample dilution by the precipitating solution, the concentration of $SrCl_2$ in the precipitating solution was adjusted to 1.0 M, and 10 µL of this precipitating solution were sufficient to effect precipitation of dodecyl sulfate ions and residual proteins from lysates obtained by incubating 10 mg of tissue in 80 µL of the lysis buffer.

Example 2

Optimization of the Spin Column Used for the Purification of gDNA From the Lysate Example 1 revealed that filtration is more effective than a simple centrifugation in removing the precipitate formed after addition of $SrCl_2$-solution. Therefore, the minimum amount of matrix necessary for gel filtration chromatography was determined using the GE-Healthcare S1000 SF matrix. The results were compared to other filtration methods, in particular filtration through a QIAshredder column (QIAGEN, Hilden, Germany), a silica frit (Mat. No: 1016844, QIAGEN, Hilden, Germany), a bed of silica particles (QiaExII, QIAGEN, Hilden, Germany), a sterile filtration through a 0.2 µm membrane of a MiniSart filter (Satorius, Göttingen, Germany), and a commercially available G25 spin column (GE-Healthcare).

10 µL of a 1 M $SrCl_2$-solution were added to 80 µL of lysates obtained as described in example 1. The mixture was incubated in an ice bath, and then applied to the different filtration devices. The mobile phase was moved through the filtration device using centrifugation, and the eluates obtained were collected and analyzed. Each experiment was carried out in duplicate. For each eluate, the amount of purified gDNA present was determined as described in the general methods. The amount of SDS was determined by UV/Vis spectroscopy according the protocol described in the general methods. Furthermore, the presence of ions in the eluates was determined by conductivity measurements according the general method. The results are presented in FIG. 3. The amount of gDNA is given in µg, the amount of SDS is given in µmol/L and the conductivity after dilution of 20 µL of the eluate with 1.980 µL water is given in µS.

Figure 3:
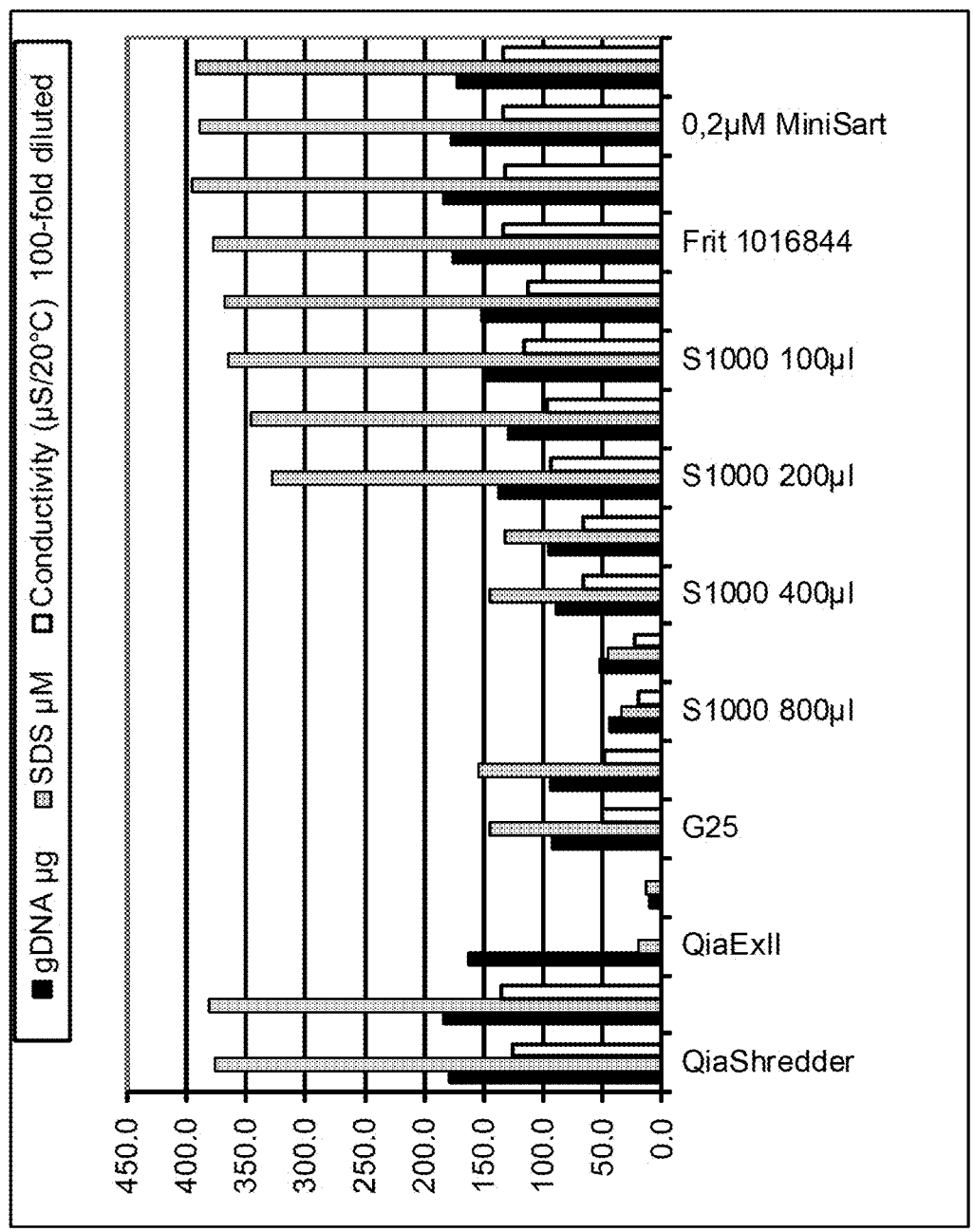
FIG. 3 shows the result of purifying lysates of 10 mg pork liver tissue previously treated with a precipitating solution, using different gel filtration resins in comparison to a simple filtration through a MiniSart filter (Sartorius, Gottingen, Germany), a silica frit (QIAGEN, Hilden, Germany), a bed of silica particles (QiaExII, QIAGEN, Hilden, Germany), or a QIA-shredder column (QIAGEN, Hilden, Germany). The effect of the purification method on the amount of gDNA (in µg), on the amount of SDS present in the eluate (in µmol/L) and on the conductivity of the eluate after dilution with water (in µS at 20° C. reference temperature) has been determined as described in Example 2.

As can be seen from FIG. 3, a conventional frit, a QIAshredder column, and a MiniSart filter are not effective in removing SDS or other salts. The commercially available G25 spin column is able to remove approximately ⅔ of the SDS present in the sample, however, the amount of residual SDS in the eluate still is too high to directly use the eluate in a subsequent PCR reaction. Using a bed of silica particles no reproducible results were obtained, the results of different experiments highly deviating from each other. In addition, the eluates obtained using the QIAshredder column and the MiniSart filter exhibited a yellow color.

Using the S1000 matrix, matrix amounts of 400 µL or less were not sufficient to form a homogenous gel bed during centrifugation using a fixed angle rotor. The minimum amount of matrix necessary to ensure homogenous gel bed formation in a spin column having a column height of 2.5 cm, and an inner diameter of 0.8 to 0.9 cm, was 600 µL.

A problem commonly observed in gel filtration chromatography using spin columns is the fact, that lysate may run down the inner walls of the spin column passing the frit without having entered the gel bed. This is in particular true, when rather large sample volumes are applied to a column, or when the sample is not applied strictly to the center of the gel bed. In consequence, the contaminants are not removed in these samples. This problem has been overcome by introducing a non-porous ring, preferably placed between the porous frit, filter, fleece or membrane and the matrix, sealing the outer area of the frit, filter, fleece or membrane, to prevent the mobile phase from entering the frit without passing the matrix.

In a next step the optimum size exclusion limit of the matrix bed was determined. 600 µL of different commercially available gel filtration matrices (SEPHACRYL® resins comprising a matrix of spherical allyl dextran and N,N'-methylene bisacrylamide) were filled into a spin column as shown in FIG. 1, equipped with a dense silica frit (Mat. No. 1017499, QIAGEN, Hilden, Germany), a plastic ring, and a screw cap. The size exclusion limits of the resins used (in base pairs, bp, or in kDa, respectively, as far as provided) are given in table 1.

TABLE 1

| Resin | Size exclusion limit |
| --- | --- |
| S-200 HR | 30 bp (5-250 kDa) |
| S-300 HR | 118 bp (10-1500 kDa) |
| S-400 HR | 271 bp (20-8000 kDa) |
| S-500 HR | 1078 bp (ND) |
| S-1000 SF | 20 000 bp (ND) |

Figure 4:
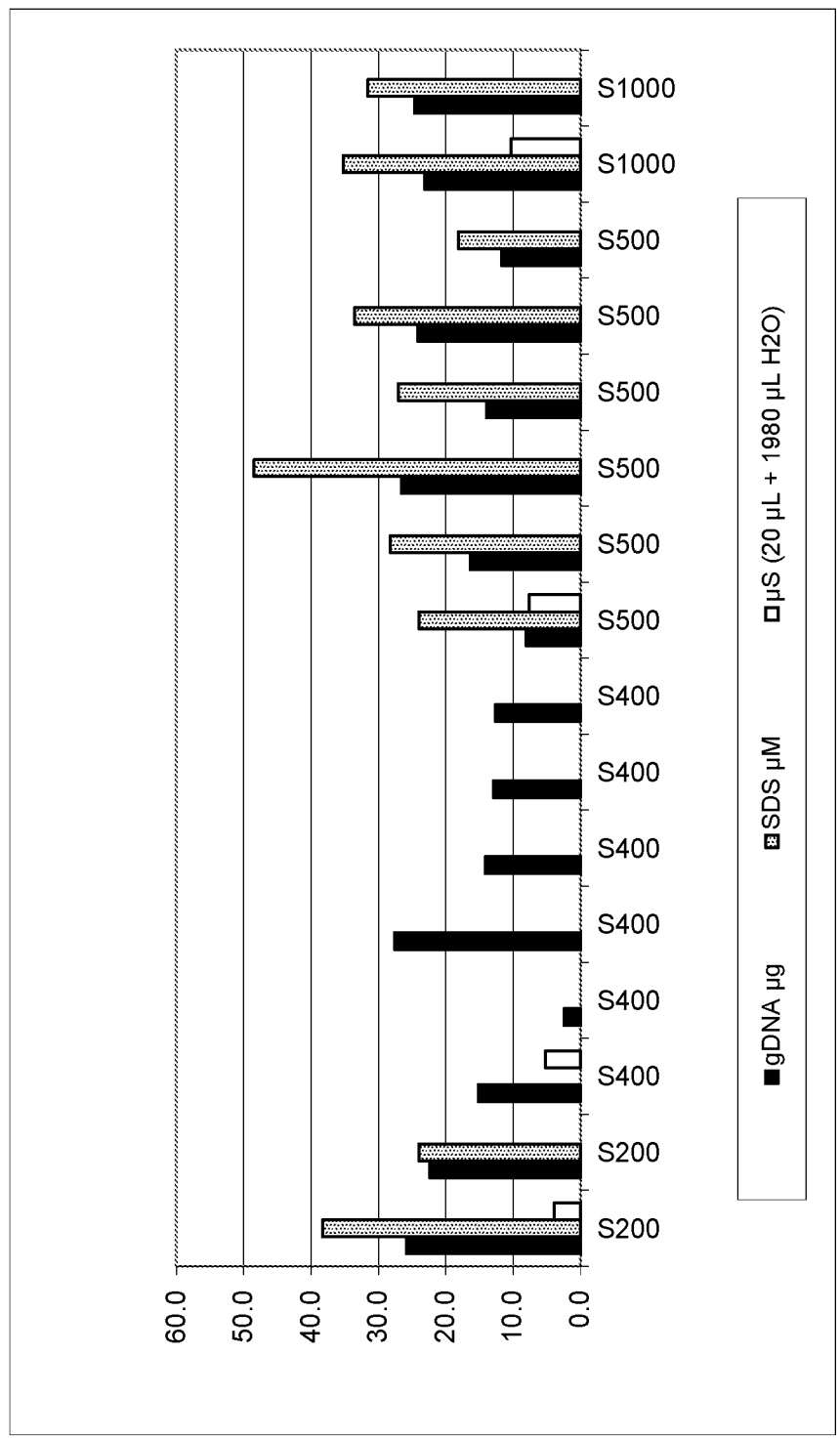
FIG. 4 shows the extent of contaminant removal by commercially available SEPHACRYL® resins of different size exclusion limits (S200, S400, S500 and S1000) according to Example 2.

All resins were equilibrated in water prior to use: 10 mL of the resin were mixed with 40 mL of water, the resin was allowed to settle, until a sediment of 10 mL was obtained, and the supernatant (water) was discarded. This procedure was repeated three times. Finally, the volume of the suspended resin was adjusted to 10 mL by the addition of water. The columns were prepared for use by establishing the gel bed in a pre-centrifugation step (pre-spinning) at 700×g for 3 min. To each column the whole lysate, obtained from 10 mg tissue as described above, including the precipitate, was applied to the center of the gel bed's upper surface. The DNA was then eluted by spinning the column at 700×g for 3 min. Each experiment was carried out at least in duplicate. The amount of gDNA and SDS present in the eluates were measured as described above. The conductivity of the samples was determined using a diluted solution of a pooled sample, wherein all samples purified using the same resin were combined. The results are depicted in FIG. 4. All resins are suitable to significantly reduce the amount of SDS and further ions present in the sample in comparison to the filtration methods discussed above. According to Goldenberger et al. (D. Goldenberger et al. *Genome Res.* 1995, 4, 368-370) SDS concentrations in a sample exceeding 345 µmol/L completely inhibit PCR reactions. For real-time-PCR reactions the tolerable maximum amount of SDS is around 250 µmol/L. Using the S400 HR resin, it was possible to completely remove SDS from the sample. This resin also proved useful in removing residual small fragments of RNA.

Example 3

PAGE Analysis of the Eluates

Figure 5:
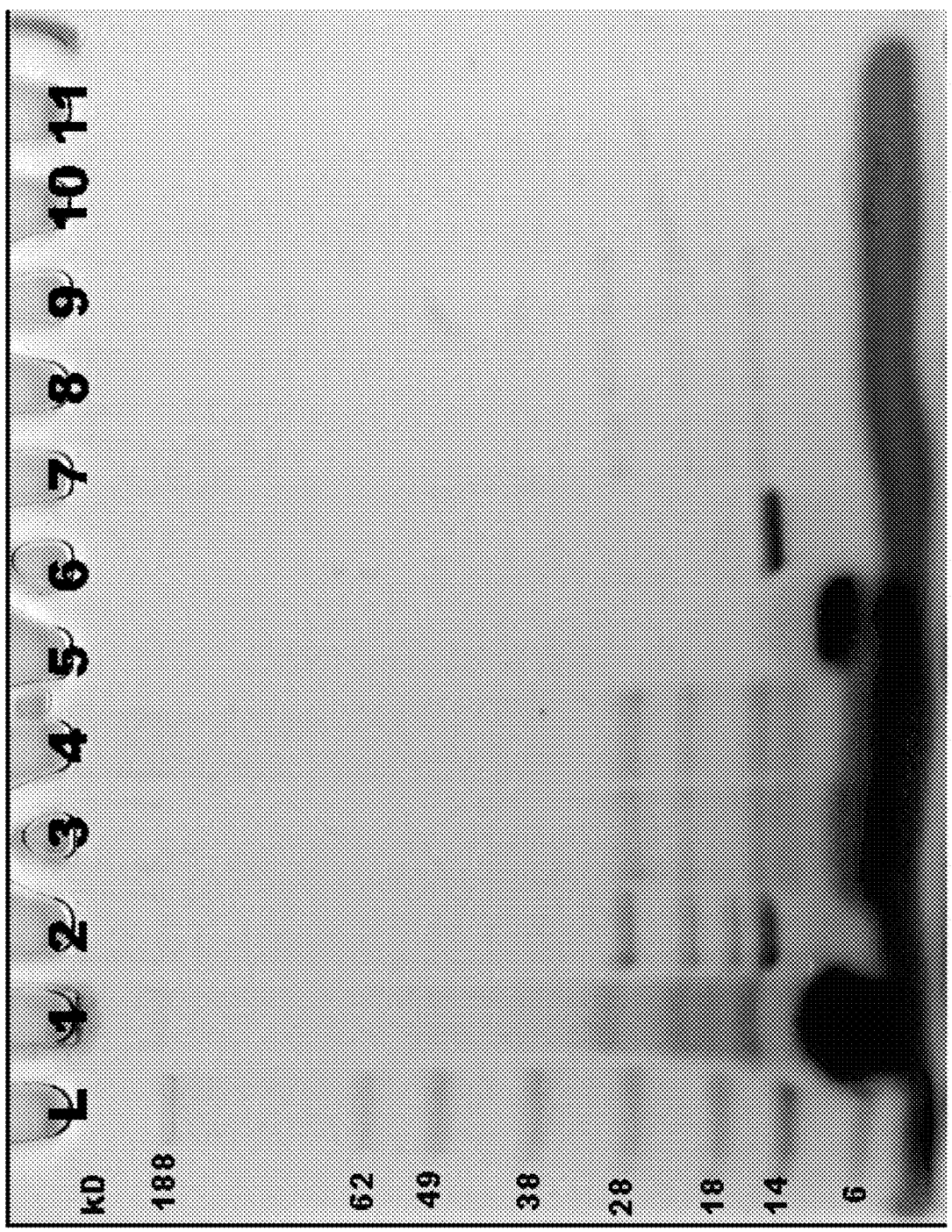
FIG. 5 shows the results as obtained according to Example 3 of a PAGE analysis of crude pork liver tissue lysate (lane 1), "precipitated" crude pork liver tissue lysate (lane 2), a lysate obtained from pork liver tissue by using the QIAamp lysis kit and RNase (lane 3), a lysate obtained from pork liver tissue by using the QIAamp lysis kit without adding RNase (lane 4), QIAGEN protease (lane 5), RNase A (lane 6), as well as eluates purified according to the present invention (lanes 7 to 9) in comparison to eluates obtained using the QIAamp kit (lanes 10 and 11). In lane L a protein standard is analyzed.

To evaluate the extent of protein removal in the purification process and to determine the residual amount of protein present in the eluate obtained after gel filtration chromatography, samples purified according to example 2 using a S400 HR resin were analyzed by PAGE analysis on a commercially available TRIS/HEPES 4-20% gradient polyacrylamide gel (LTF-LABORTECHNIK), containing SDS. The gel was run at 100 volt for 25 min in the supplied TRIS/HEPES buffer using the NOVEX XCell II system (Invitrogen GmbH, Karlsruhe, Germany). 15 µL of the samples spiked with a protein size marker were diluted with 15 µL of the 2× buffer, provided with the gel. The mixture was heated to 95° C. for 5 min, then cooled in an ice bath, and afterwards loaded into the gel pocket. The gel was stained overnight by immersing it into Gradipore stain (Gradipore, Sydney, Australia), and then rinsed with water. The results are presented in FIG. 5. The lane named "L" is a SeaBlue protein standard from Invitrogen (Karlsruhe, Germany). In lane 1, 15 µL of the crude lysate obtained from 10 mg pork liver tissue using the lysis buffer described above were analyzed. In lane 2, 15 µL of the same lysate were analyzed after addition of the precipitating solution described above (without filtration step). For comparison, in lane 3 15 µL of a lysate obtained using the QIAamp Kit, additionally treated with 15 µL Rnase A, were analyzed. In lane 4, 15 µL of a lysate obtained using the QIAamp kit without adding RNase were analyzed. For comparison, the QIAGEN Protease and RNase A were analyzed in lanes 5 and 6, respectively. In each of lanes 7 to 9, aliquots of 20 µL of the eluates, obtained after purification by gel filtration chromatography according to the present invention, were analyzed (in total, 100 µL eluate were obtained). In lanes 10 and 11, an aliquot of 20 µL of the eluates obtained by using the QIAamp kit were analyzed. (in total, 400 µL eluate were obtained). It can be seen that a large amount of proteins is already co-precipitated together with SDS by the addition of strontium chloride. The remaining amount of protein can be removed efficiently by gel filtration chromatography according to the present invention, and the results obtained using the method of the present invention are comparable to the results obtained using the commercially available QIAamp kit, especially when keeping in mind, that the dilution of the eluate obtained from the QIAamp kit is four times higher. The results obtained from lung samples and mouse tails were comparable (data not shown).

Example 4

AEX-HPLC Analysis of the Eluate

To detect minute amounts of residual contaminants such as proteins and RNA fragments, an anion exchange (AEX) HPLC analysis was performed on an TMAE-Fractogel S HPLC column using a $CaCl_2$ gradient at pH 7.2 at a flow rate of 1.5 mL/min. A gradient ranging from 0 mmol/L $CaCl_2$ to 300 mmol/L $CaCl_2$ in water, comprising 5% TRIS (pH 7.2), over 35 column volumes was established. As an injection volume 200 µL were used.

Figure 6:
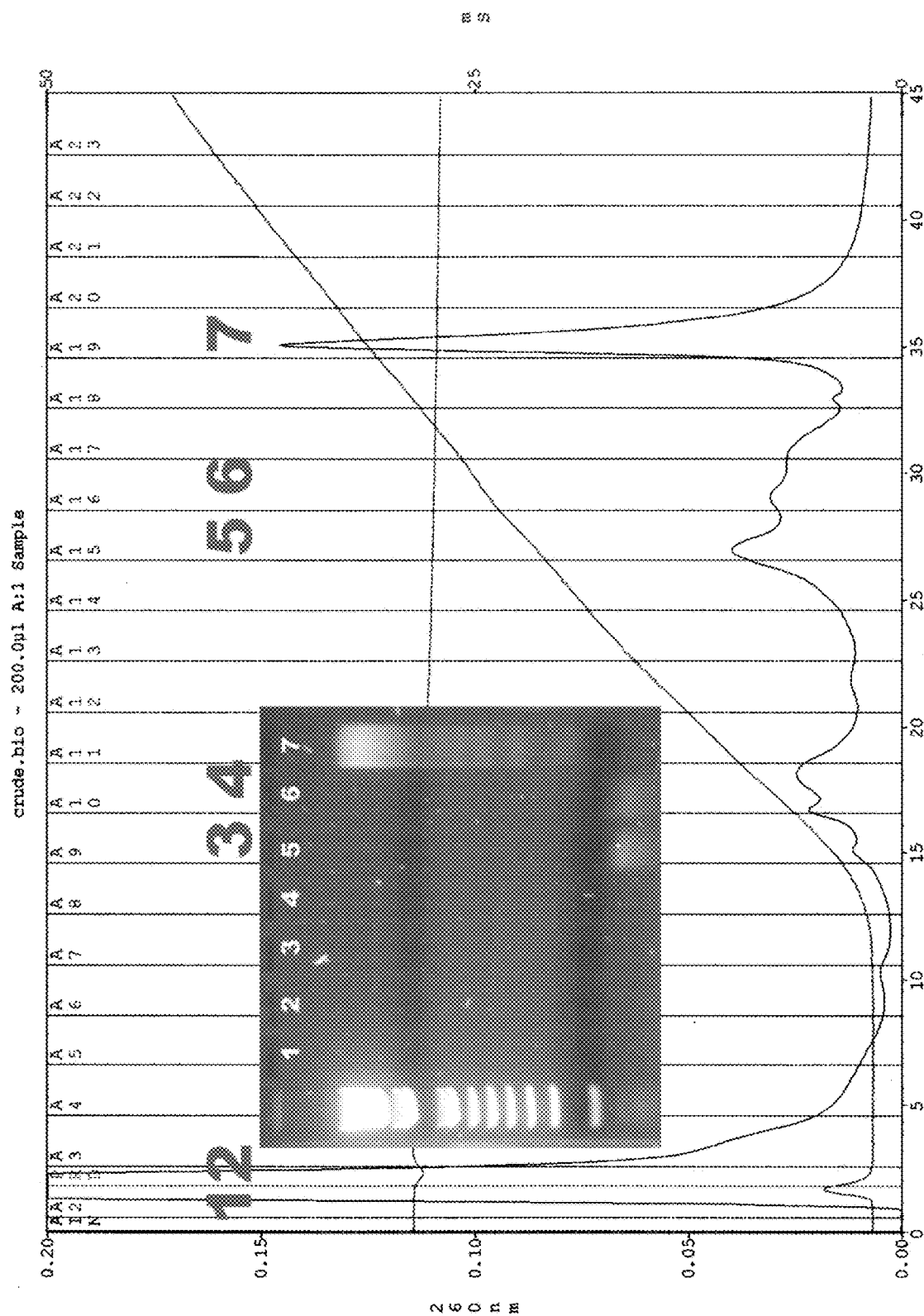
FIG. 6 shows the AEX-HPLC analysis of 200 µL of crude pork liver lysate obtained without adding RNase according to Example 4. Furthermore, an agarose gel analysis of the different fractions collected from the HPLC run is shown.

In a first experiment 200 µL of the crude lysate obtained from incubating 10 mg pork liver tissue with the buffer described above in the absence of RNase were analyzed. Seven fractions were collected from the HPLC, reacted with the dye Stains-All according to the general method, and subsequently analyzed on agarose gel. The HPLC chromatogram and the photograph of the agarose gel are depicted in FIG. 6.

Fraction 1 and 2 did not react with the dye, indicating concentrations of SDS and nucleic acids below the detection limit of 21 µmol/L SDS. Fraction 3 and 4 exhibited a blue color upon addition of the dye, indicating the presence of nucleotides or soluble proteins, which cannot be stained with SYBR-Green II on an agarose gel. Fraction 5 and 6 were eluted at conductivities typical for RNA, and gave a faint band of nucleic acid smaller than 100 bp in the agarose gel, while fraction 7 contained the genomic DNA.

Figure 7:
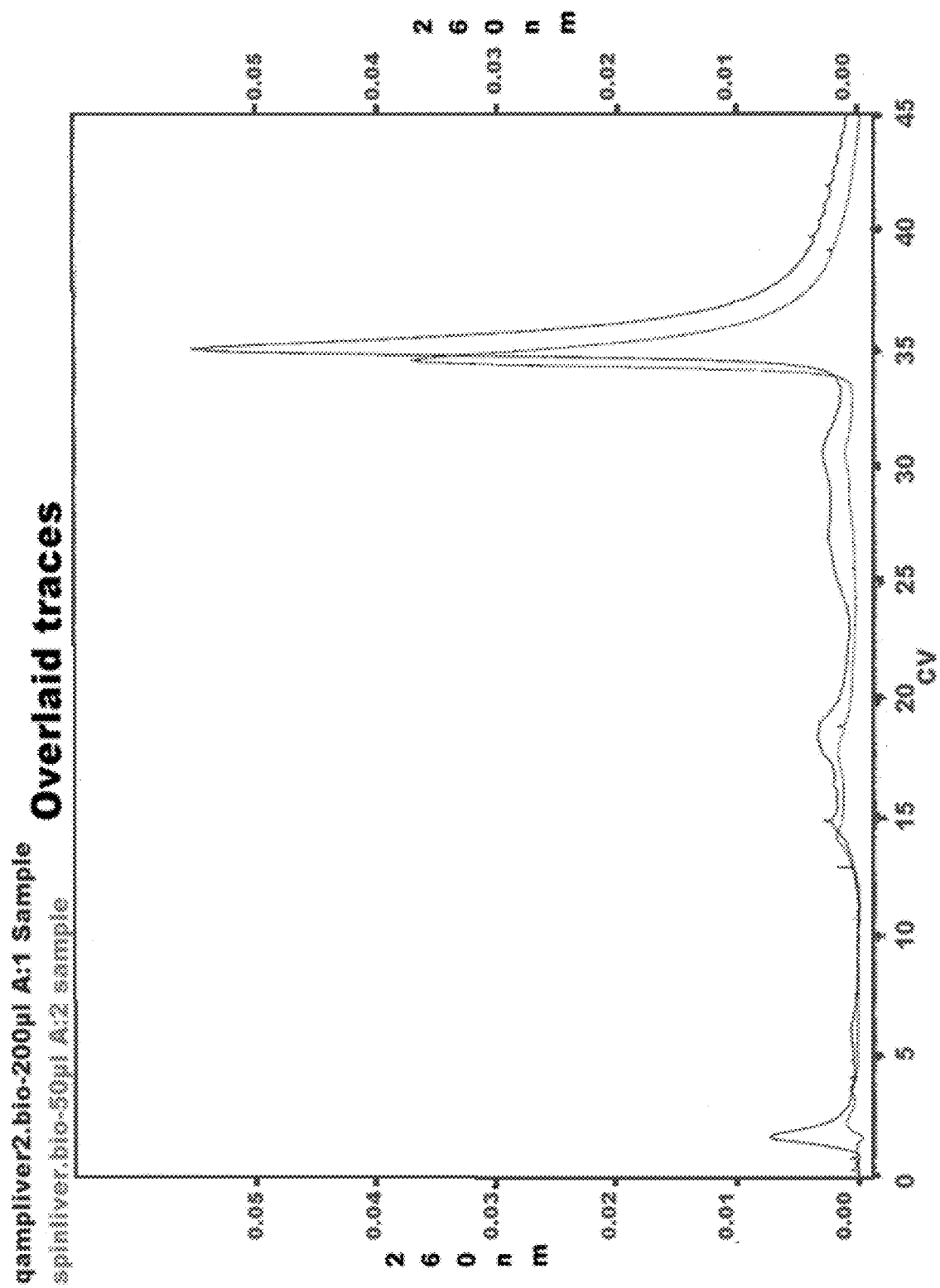
FIG. 7 shows a comparison of the HPLC profiles obtained from the eluates of samples of 10 mg fresh pork liver, purified using either a) the method of the present invention, and b) the QIAamp kit (QIAGEN, Hilden, Germany) (see Example 4). While the amount of residual contaminants is comparable in both samples, the yield of gDNA obtained by the method of the present invention is almost 50% higher (9.2 µg versus 6.2 µg), as determined using a calibration curve.

In further experiments, samples purified using the device and method of the present invention were compared to samples purified using the commercially available QIAamp kit by HPLC analysis. To determine the amount of genomic DNA, a calibration curve using increasing amounts of genomic E. coli DNA, purified by anion exchange chromatography, was used, correlating the area under curve (AUC) of the gDNA elution peak with the amount of gDNA loaded onto the column. In FIG. 7 the overlaid chromatograms of a sample purified using the present invention (a) and a sample purified using the QIAamp Kit (b) are presented, both traces were monitored at a wavelength of 260 nm. The yield obtained from 50 µL of the eluate purified according to the present invention (trace a in FIG. 7) is significantly higher compared to the amount of gDNA obtained from 200 µL eluate obtained by using the QIAamp Kit. (For comparison, traces a and b in FIG. 7 are normalized to a common injection volume.) This demonstrates that a high concentration of gDNA in the eluate can be achieved using the purification method of the present invention. The amount of residual proteins and other impurities were comparable in both samples, as determined by integration of the respective peaks in the HPLC chromatogram. The amount of gDNA, present in the sample purified according to the present invention, was 9.2 µg, determined using the calibration curve, while the amount of gDNA obtained by using the QIAamp Kit was 6.2 µg.

Example 5

Figure 8A:
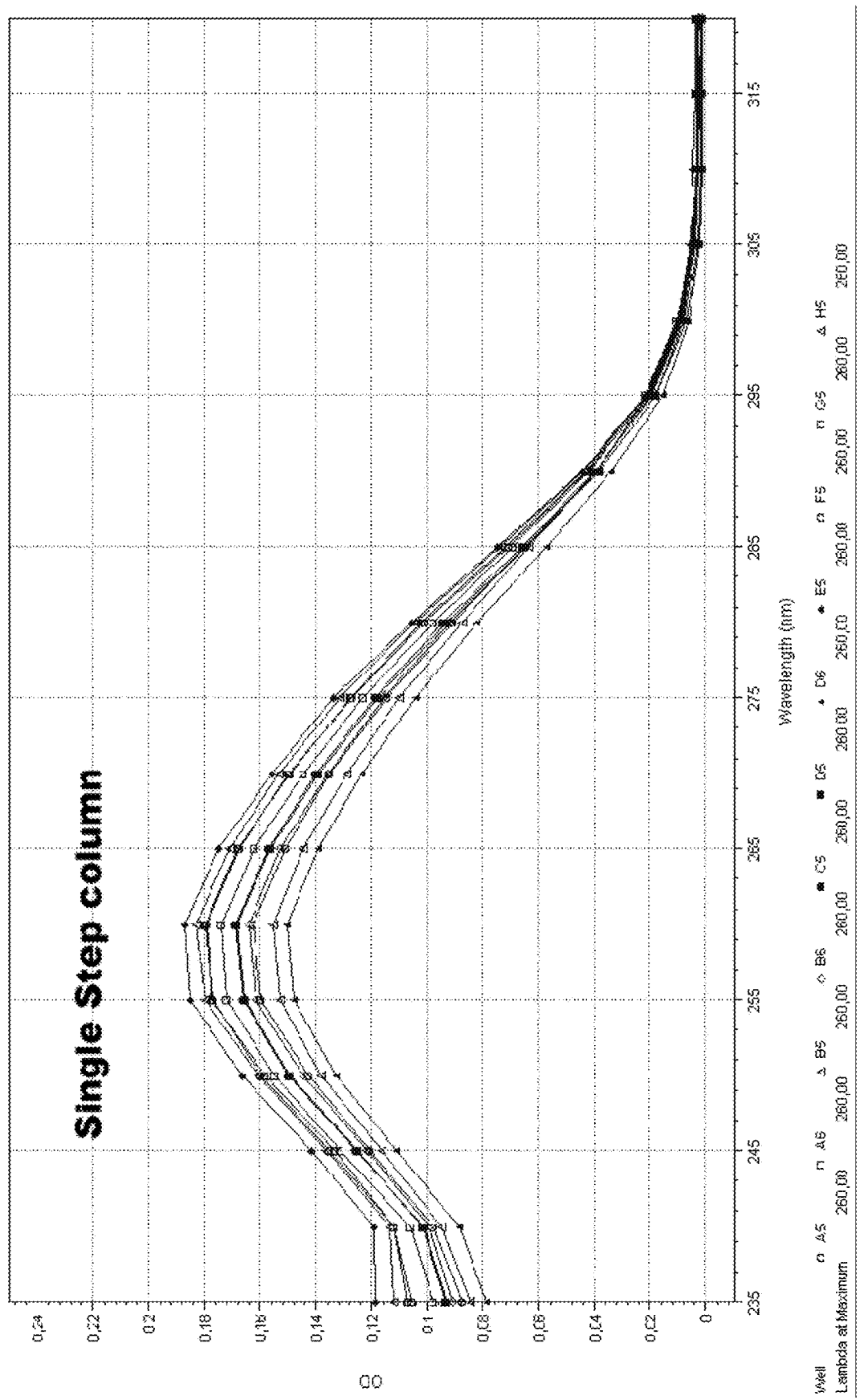
FIGS. 8a and 8b show the UV/Vis spectra of gDNA eluates, obtained by lysing and purifying 10 mg pork liver tissue, using the method of the present invention (upper spectrum), and using the QIAamp kit (lower spectrum), respectively (see Example 5).
Figure 8B:
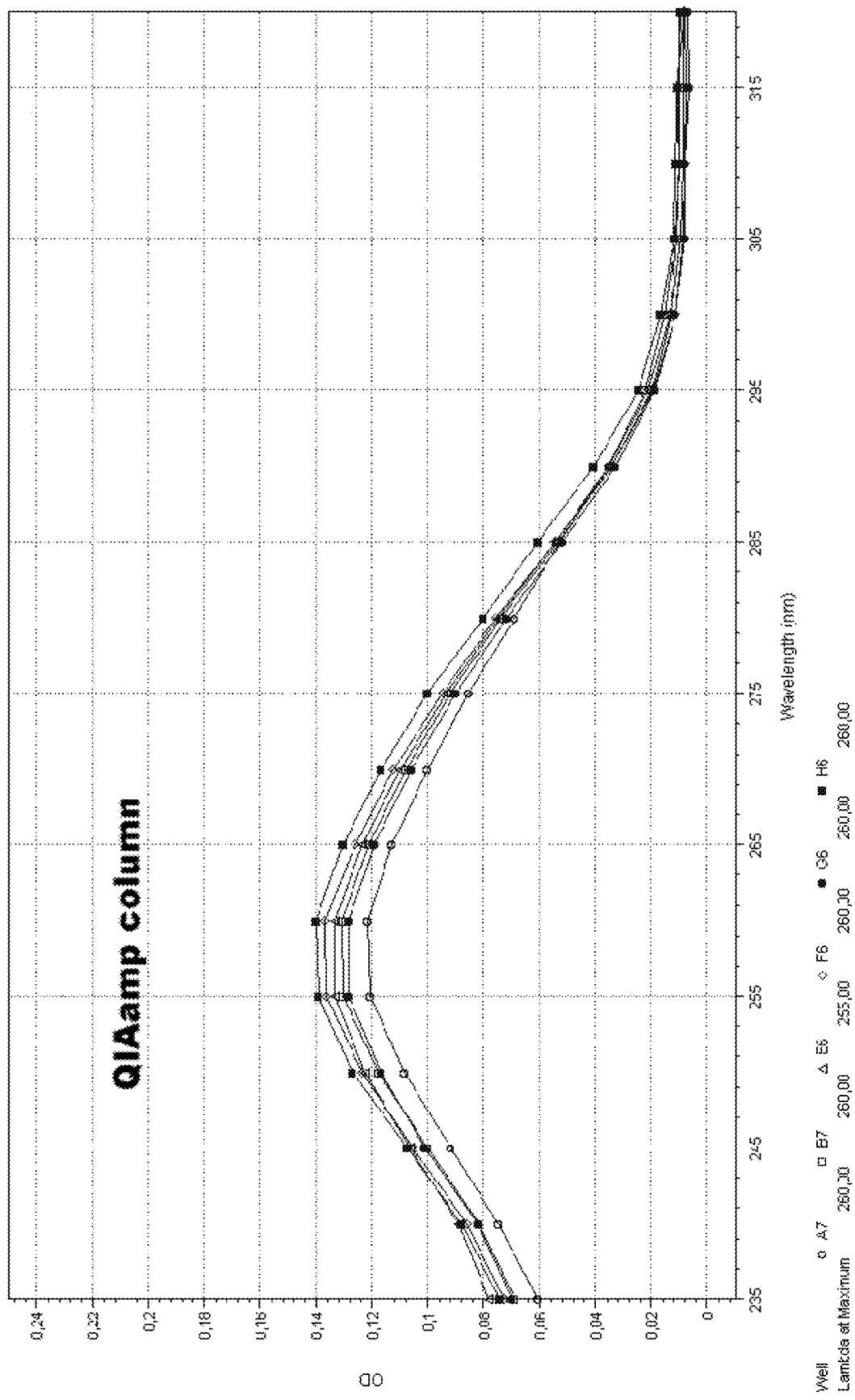

Determination of Yield and Purity of the gDNA in the Eluates Using UV/Vis Spectroscopy 12 samples of 10 mg pork liver were lysed and purified according to the method of the present invention using water as eluent in the gel filtration step, and compared to 6 samples of 10 mg pork liver purified using the QIAamp columns with the same eluent. The results are shown in FIG. 8, supporting the results obtained by HPLC analysis. The absorbance at a wavelength of 260 nm, where gDNA has its absorbance maximum, was always higher in the samples purified by the method according to the present invention than in the QIAamp purified samples. In addition, the baseline is elevated in the spectra of the QIAamp purified samples in comparison to the baseline in the spectra of the samples purified according to the present invention, which may indicate a higher amount of residual solid particles in the QIAamp purified samples.

Example 6

RT-PCR Analysis of Purified Rat Tail gDNA

Figure 9:
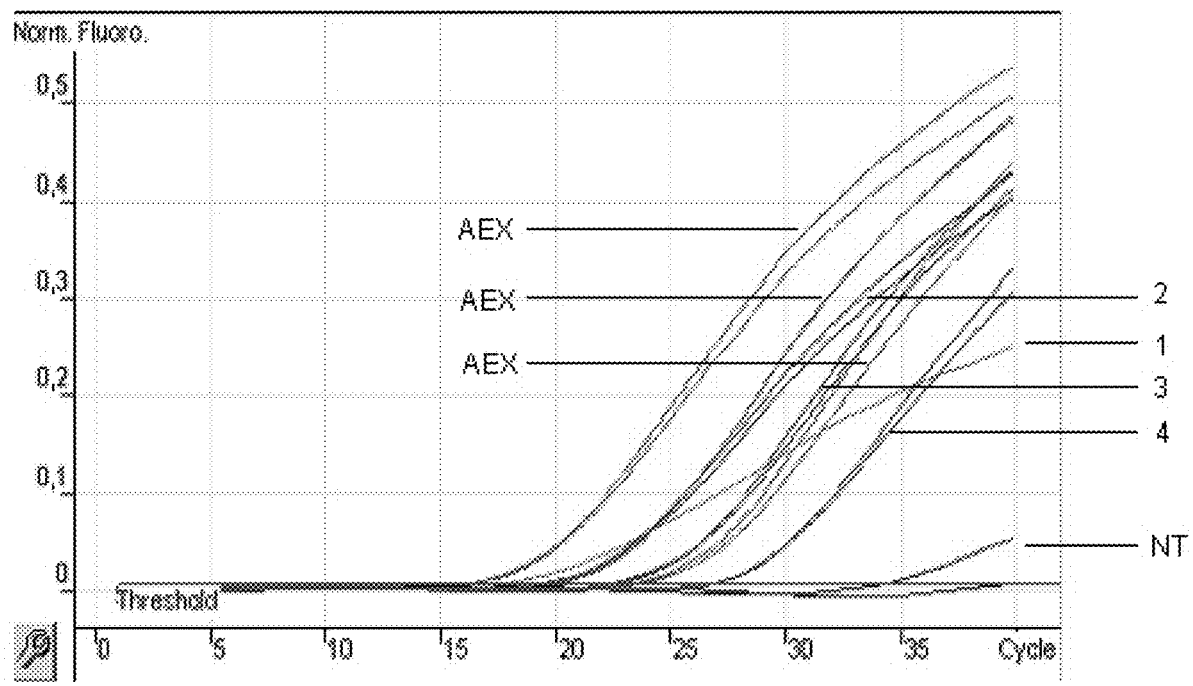
FIG. 9 shows an inhibition study (jun assay) (see Example 6) of samples isolated and purified from rat tail, using the method of the present invention. Due to the high concentration of gDNA present in the sample, a strong product inhibition is observed in the undiluted sample, and even a weak inhibition is observed in the sample which was diluted tenfold, while no inhibition was observed for samples with higher dilution.

To ensure that no PCR inhibitors are present in the samples purified according to the present invention, samples of 20 mg rat tail were lysed as described above and purified according to the method of the present invention as detailed above. These purified samples were then analyzed in a real time PCR (RT-PCR) using the jun-system on the Rotorgene system (Corbett, Sydney, Australia) and compared to the results obtained using gDNA using AEX chromatography. A commercially available primer/probe system (FAM-TAMRA, Applied Biosystems, Darmstadt, Germany), including a 20× jun PCR primer/probe mix was used in combination with an 2× TaqMan PCR universal master mix from Applied Biosystems. The RT-PCR was carried out according to the manufacturer's instruction. In particular, polymerase activation was carried out by heating the mixture for 20 min to 95° C., cycling was performed by melting the duplexes at 95° C. for 15 seconds, and annealing was carried out at 60° C. for 60 seconds. In total, 40 cycles were performed. The reaction mixture consisted of 22.5 µL of the gDNA-containing sample, 25 µL of the master mix and 2.5 µL of the primer mix. Samples purified according to the present invention were used in an undiluted form and after dilution with water (factor 10, 100 and 1000) as a template in the PCR. Even though the undiluted sample (curve 1 in FIG. 9) showed a rather strong product inhibition due to the high concentration of gDNA in the sample, it was possible to amplify the sequence of the all samples purified by the method of the present invention, regardless of the dilution factor. The sample which had been tenfold diluted with water (curve 2) exhibited only a weak inhibition. No inhibition was observed in the samples which had been diluted 100-fold or 1000-fold prior to amplification (curves 3 and 4), respectively. For comparison, the reaction was also performed in the absence of target (no target reaction, NTC), and three samples purified by AEX chromatography were amplified under the same conditions, too.

Figure 10:
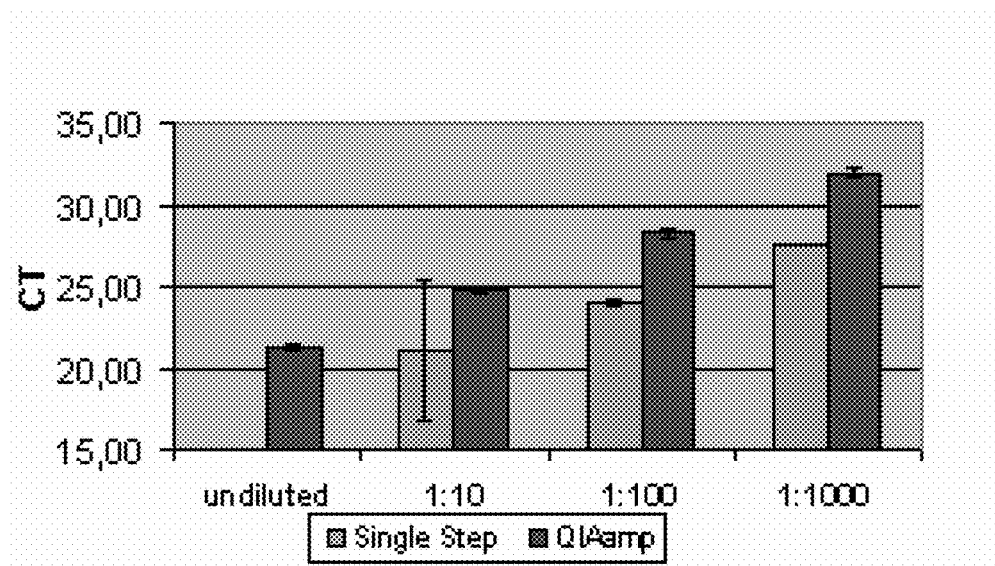
FIG. 10 shows the CT-values obtained according to Example 6 from a qRT-PCR reaction amplifying the lysate obtained from 10 mg rat liver tissue using the method of the present invention (denoted as "single step"), and using the QIAamp kit in a jun assay on a TaqMan 7700 analyzer. Again a product inhibition was observed in the undiluted and in the tenfold diluted samples purified with the method of the present invention. However, with diluted samples the CT-values were always lower for the lysates obtained according to the method of the present invention.

Similar results were obtained with samples derived from 10 mg frozen liver tissue, lysed as described above and purified according to the present invention in comparison to samples lysed and purified using the QIAamp kit. FIG. 10 shows a comparison of the CT-values obtained in RT-PCT of these samples in a jun essay using different dilutions of the purified samples. Again, a product inhibition is observed in the reaction using the undiluted samples purified by the present invention. The CT-values obtained from 10-fold, 100-fold and 1000-fold diluted samples, respectively, purified according to the present invention are always lower than the CT-values obtained using the QIAamp purified samples, indicating a higher amount of gDNA present in the samples purified according to the present invention.

Example 7

Comparison of the Yield of gDNA Obtained from Different Tissue Samples by the Method of the Present Invention and by Using the QIAamp Kit Samples of the different tissues listed in Table 2 were lysed as described above and SDS was subsequently precipitated from the lysate by adding strontium ions, or the samples were lysed according the QIAamp protocol. After lysis (and precipitation of dodecyl sulfate ions where applicable), the samples obtained from the same kind of tissue by the same purification method were pooled, and then split into 100 μL aliquots. These aliquots were purified according to the method of the present invention or according to the QIAamp protocol, respectively. The amount of gDNA present in the sample was analyzed by UV/Vis spectroscopy and/or HPLC analysis. The average results obtained are given in Table 2.

TABLE 2

| Sample | yield [μg] present invention | yield [μg] QIAamp | detection method |
|---|---|---|---|
| 10 mg pork liver | 18.3 | 12.4 | HPLC |
| 10 mg mouse lung | 6.9 | 4.3 | UV/Vis |
| 20 mg mouse tail | 18.5 | 6.5 | UV/Vis |
| 10 mg mouse kidney | 25.5 | 8.7 | UV/Vis |
| 5 mg mouse spleen | 36.6 | not determined | UV/Vis |
| 10 mg mouse spleen | 66.0 | not determined | UV/Vis |
| 10 mg rat tail | 8.7 | 6.5 | UV/Vis |
| 20 mg rat tail | 11.7 | not determined | HPLC |
| 10 mg pork muscle | 5.8 | 1.5 (0.5) | UV/Vis (HPLC) |
| 50 mg bovine pancreas | 4.5 | 0 | UV/Vis |
| 10 mg rat liver | 30.2 (4.6) | 4.6 (2.0) | UV/Vis (HPLC) |

Example 8

Lysis and Purification of Human Blood Samples

Figure 11:
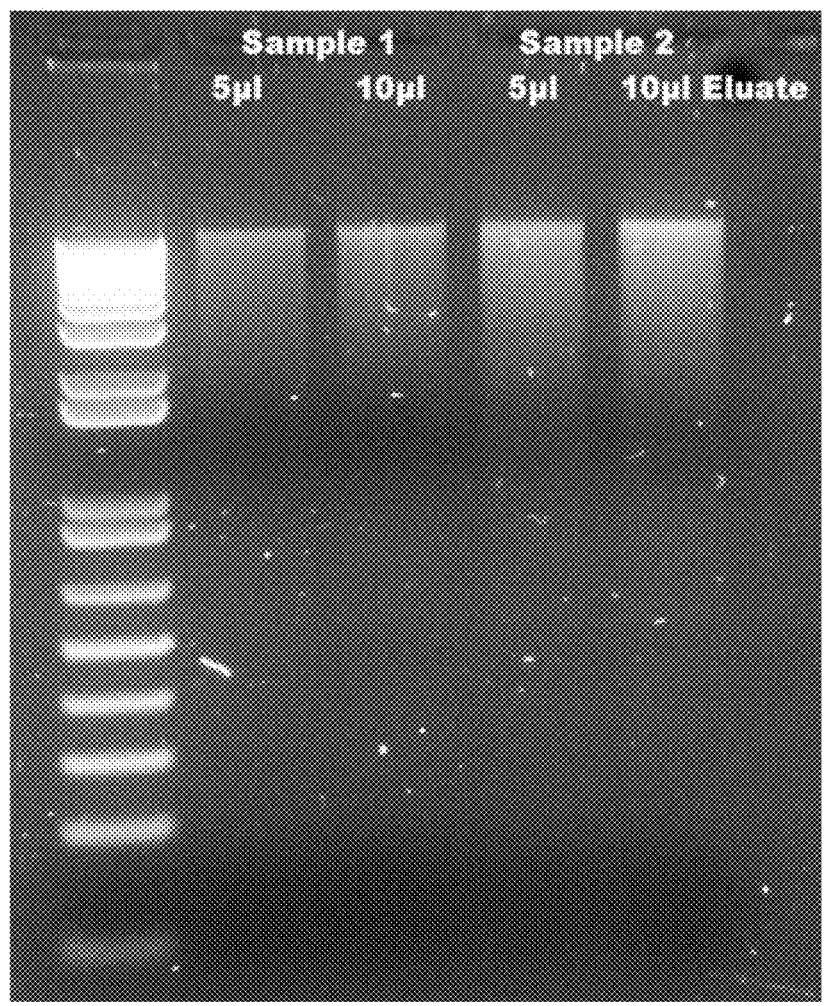
FIG. 11 shows a SYBR-green II stained agarose gel of two blood samples purified by the method of the present invention (see Example 8). As a reference, a DNA length standard (GIBCO 1 kb plus DNA ladder, Invitrogen GmbH, Karlsruhe, Germany) is shown on the left hand side.

Due to the high liquid content of blood samples, a twofold concentrated lysis buffer (2×) comprising 50 mmol/L TRIS and 50 mmol/L SDS, adjusted to pH 8.5 by the addition of $H_2SO_4$, was used for lysis of the cells. Two samples of 40 μL of human blood from the same donor were mixed with an equal amount of the 2× lysis buffer. Blood proteins were then depleted by addition of 10 μL QIAGEN Protease (2.5 AU/ml). The samples were incubated at 62° C. for 10 min. SDS was removed from the lysates by precipitation as described above, and the samples were purified by gel filtration chromatography using the spin columns of the present invention. Aliquots of 5 μL and 10 μL were then analyzed on an agarose gel (FIG. 11). The gDNA band is visible in all samples analyzed, and no shorter fragments can be detected.

Quantification of the amount of gDNA present within the samples revealed an average yield of 600 ng gDNA in the samples using 18S gDNA primers (for each of the two samples RT-PCR was carried out in duplicate, and the amount of gDNA was determined as an average value from all four experiments).

Example 9

Figure 12:
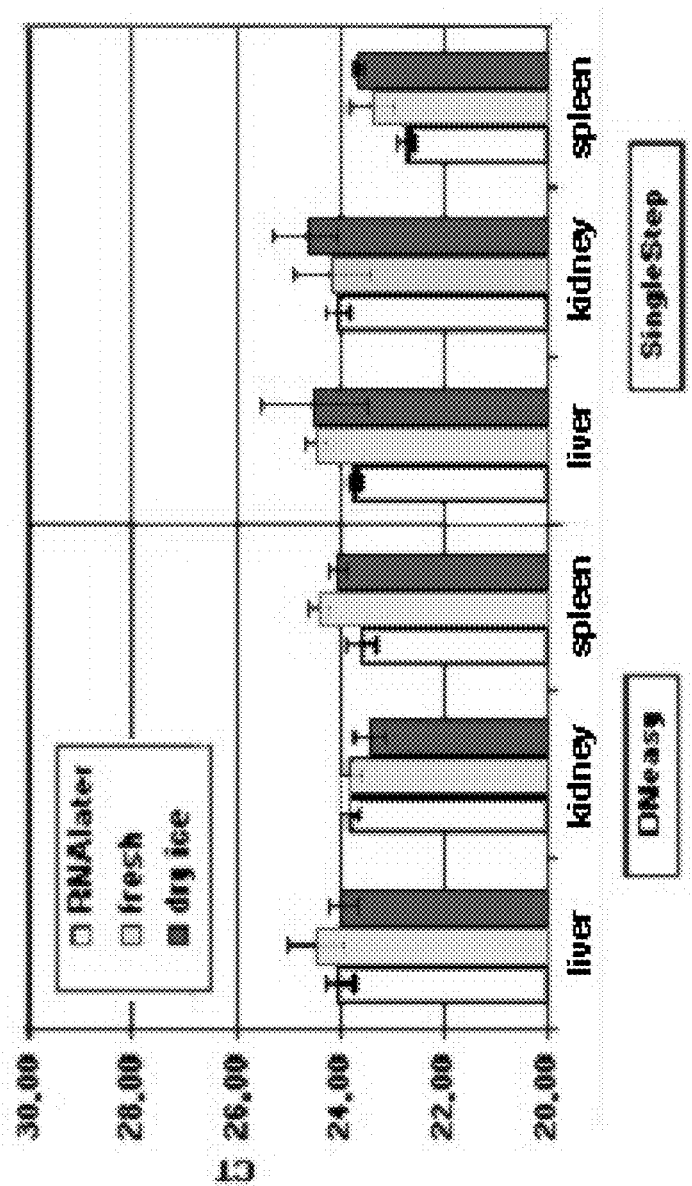
FIG. 12 shows a comparison of the RT-PCR results obtained from liver, kidney and spleen tissue samples, either stored in the commercially available RNA later reagent (QIAGEN, Hilden, Germany), being frozen on dry ice (−78° C.) prior to use, or used as received (fresh sample). The samples were lysed and purified using the commercially available DNeasy kit (QIAGEN, Hilden, Germany) (left hand side), and the method of the present invention (right hand side, denoted as "single step") as described in Example 9. It can be seen that the CT-values obtained in the RT-PCR reaction are comparable for both methods.

RT-PCR of Different Animal Tissue Samples 50 ng (as estimated by UV/Vis spectroscopy) of purified gDNA obtained from rat liver, kidney and spleen tissue lysed as described above and purified using the method of the present invention, or according to the DNeasy protocol using a commercially available DNeasy kit (QIAGEN, Hilden, Germany) were used as targets for RT-PCR. Fresh and frozen tissue samples, and samples stabilized in the commercially available RNA later reagent (QIAGEN, Hilden, Germany) were used. The samples were then analyzed in a SYBR-Green-based RT-PCR reaction on a TaqMan system. As can be seen in FIG. 12, the CT-values obtained in the RT-PCR reaction are comparable for both methods, regardless of the kind of sample analyzed (fresh, frozen and stabilized in RNA later, respectively). Buffer AE, comprising 10 mmol/L TRIS/HCl and 0.5 mmol/L EDTA, adjusted to pH 9.0, was used to equilibrate the spin columns according to the procedure described above and as an eluent.

Example 10

Figure 13:
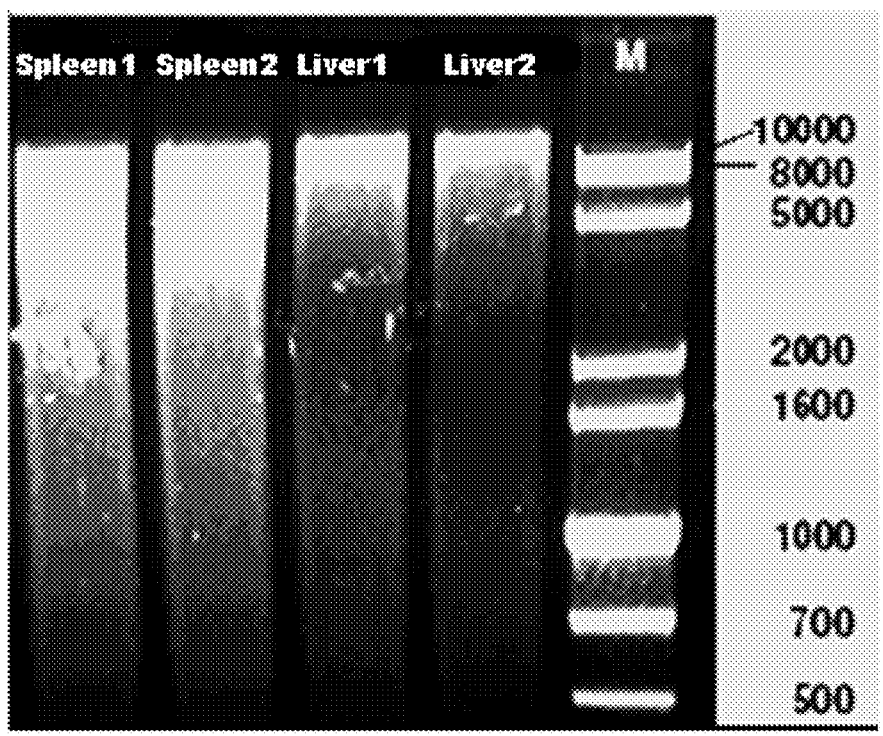
FIG. 13 shows an agarose gel of the eluates obtained from lysis and purification of liver and spleen tissue according to the present invention (see Example 10).

Purification of High Molecular Weight gDNA From Liver and Spleen Samples 20 mg of rat liver and spleen tissue, respectively, were lysed as described above and purified according to the present invention. Lysis was complete within 30 min. Each experiment was carried out in duplicate. Quality of gDNA in the lysates obtained were analyzed in a PCR reaction and on an ethidium bromide stained agarose gel (FIG. 13), which clearly shows a gDNA band of high molecular weight, even though the gel was overloaded. The amount of gDNA present in the samples as well as the purity, estimated by the ratio of the absorbance of the sample at a wavelength of 260 nm to the absorbance at a wavelength of 280 nm are presented in Table 3. High amounts of gDNA of good purity were obtained, even though reaction conditions were not finally optimized.

TABLE 3

| Sample | ng DNA/ μL eluate | A260 | A260/A280 |
|---|---|---|---|
| liver 1 | 654.29 | 3.089 | 1.84 |
| liver 2 | 621.75 | 12.44 | 1.72 |
| spleen 1 | 1330.87 | 26.62 | 1.85 |
| spleen 2 | 1494.49 | 29.89 | 1.82 |

Example 11

Comparison of Different Column Buffers

Figure 14:
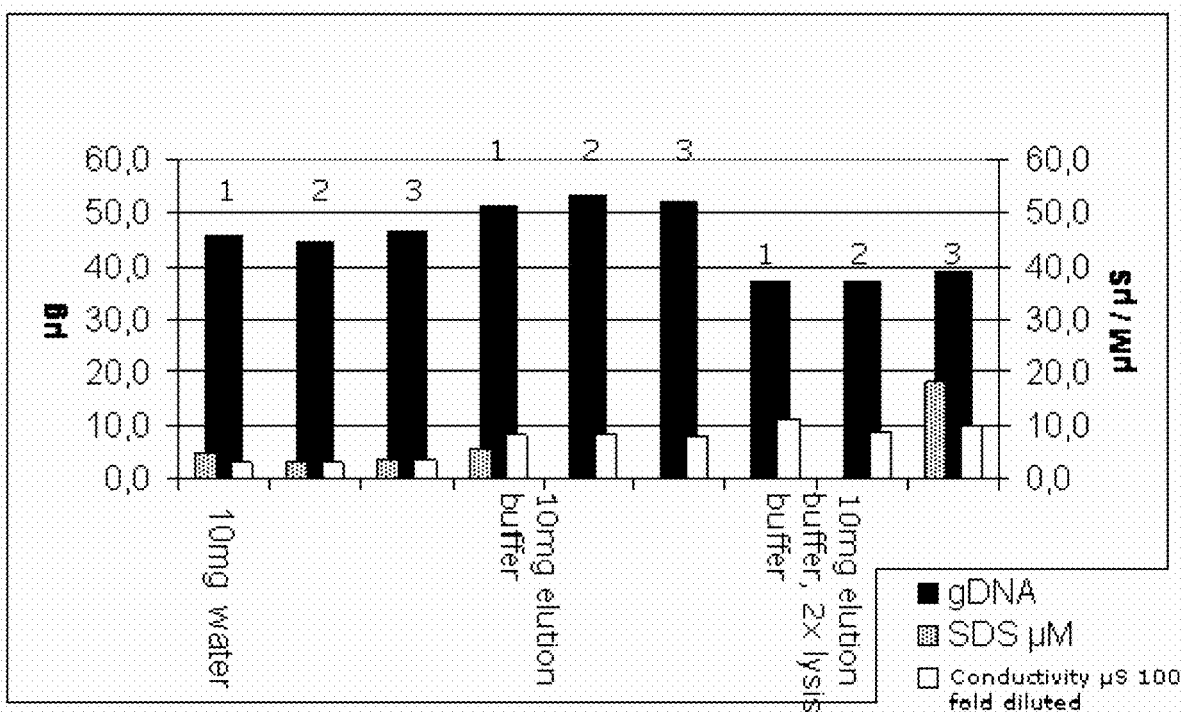
FIG. 14 shows the amount of gDNA (in μg) and SDS (in μM) and the conductivity (in μS after dilution) in the eluates obtained from lysis and purification of rat liver tissue according to the present invention using water, buffer AE and a twofold concentrated buffer AE as an eluant in the gel filtration step as shown in Example 11.

Samples of 10 mg of frozen rat liver tissue each were lysed as described above. After addition of the precipitating agent the samples were purified by gel filtration chromatography, using the columns of the present invention, equilibrated in water and buffer AE, respectively. In addition, several samples were lysed in a double concentrated lysis buffer and purified by gel filtration chromatography using the spin columns of the present invention, equilibrated in buffer AE. The eluates obtained were analyzed by gel electrophoresis and the amount of gDNA, and SDS as well as the conductivity of the eluates were determined. SDS was only detected in two samples. The results are presented in FIG. 14.

Example 12

Isolation and Purification of gDNA From FFPE-Tissue Samples

Samples of 10 μm thickness from a formalin fixed paraffin embedded (FFPE) block of rat liver were lysed, and the gDNA was isolated and purified using a) a commercially available QIAamp kit (QIAGEN, Hilden, Germany) and b) the method and device according to the present invention.

a) Three sections with each 10 µm from the FFPE block were lysed in 1 mL xylene, mixed by vortexing for 10 s, and centrifuged at full speed for 2 min. The supernatant was removed by pipetting. Residual xylene was extracted by adding 1 mL EtOH to each sample, vortexing the samples for 10 s, centrifuging them at full speed for 2 min and removing the supernatant. The open tubes containing the samples were incubated at room temperature for 20 min to evaporate residual EtOH. The pellets obtained were resuspended in 180 µL buffer ATL (QIAGEN, Hilden, Germany). To each sample 20 µL of Proteinase K (2.5 AU/ml) (QIAGEN, Hilden, Germany) were added, and the samples were mixed by vortexing. The samples were incubated at 56° C. for 1 h before incubating them at 90° C. for 1 h. The samples were cooled to room temperature, then 1 µL of RNase A (10 U/ml) (QIAGEN, Hilden, Germany) was added to each sample. 200 µL buffer AL (QIAGEN, Hilden, Germany) was added to each lysate, and the samples were mixed thoroughly by vortexing. 200 µL EtOH were then added, and the samples were vortexed again. The lysates were transferred to a QIAamp MinElute column (QIAGEN, Hilden, Germany) and centrifuged at 6000×g for 1 min. The QIAamp MinElute column was placed into a clean 2 mL collection tube and the flow-through was discarded. The column was opened and washed with 500 µL buffer AW1 (QIAGEN, Hilden, Germany) and centrifuged at 6000×g for 1 min. The QIAamp MinElute column was placed into a clean 2 mL collection tube and the flow-through was discarded. The column was opened again and washed with 500 µl buffer AW2 (QIAGEN, Hilden, Germany) and centrifuged at 6000×g for 1 min. The QIAamp MinElute column was placed into a clean 2 mL collection tube and the flow-through was discarded. The membrane was centrifuged at full speed for 3 min to remove traces of buffer. Elution of the gDNA was done in a clean 1.5 ml micro centrifuge tube with 100 µl RNase-free water by incubation at room temperature for 1 min and centrifugation at full speed for 1 min.

b) Three sections with each 10 µm thickness from the FFPE block were lysed in 80 µL of the lysis buffer described above (25 mmol/l Tris/H$_2$SO$_4$, 25 mmol/L SDS, pH 8.5), supplemented with 10 µL QIAGEN Protease (2.5 AU/ml) (Hilden, Germany) and 1 µL RNase A (7000 U/ml). The samples were mixed by vortexing. Three samples were incubated at 62° C. for 30 min and then at 90° C. for 1 h, while the other three samples were incubated at 56° C. for 1 h before incubating them at 90° C. for 1 h. To each sample 10 µL of precipitating solution (1 mol/L SrCl$_2$) was added, and the samples were mixed by vortexing and incubated on ice for 10 min. Each sample was then transferred to a pre-spun spin column according to the present invention ("single-step column"), and the column was centrifuged at 700×g for 3 min, while the eluate containing the gDNA was collected.

Figure 15:
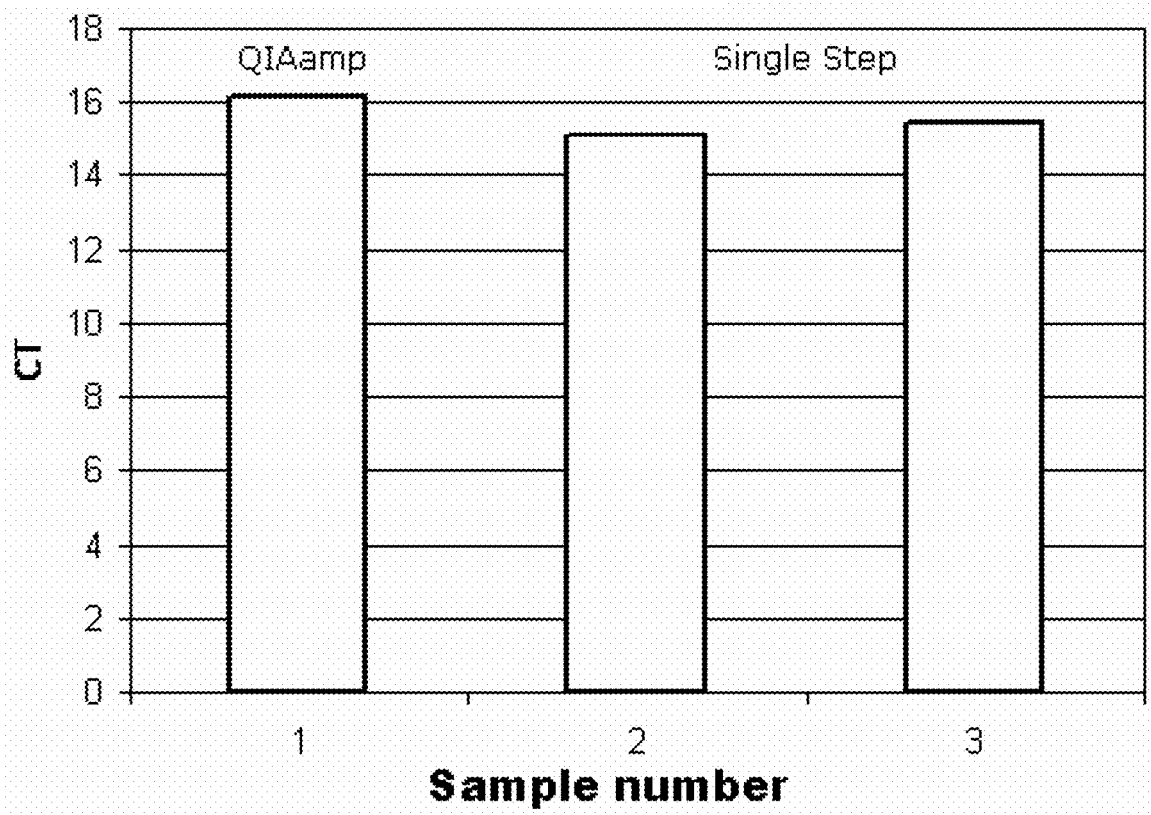
FIG. 15 shows the CT-values of an RT-PCR of a gene coding for 18S rRNA from FFPE rat liver tissue (Example 12). Sections from the FFPE block were lysed and purified using a commercially available kit (1) and the method and device of the present invention (2 and 3).
Figure 16:
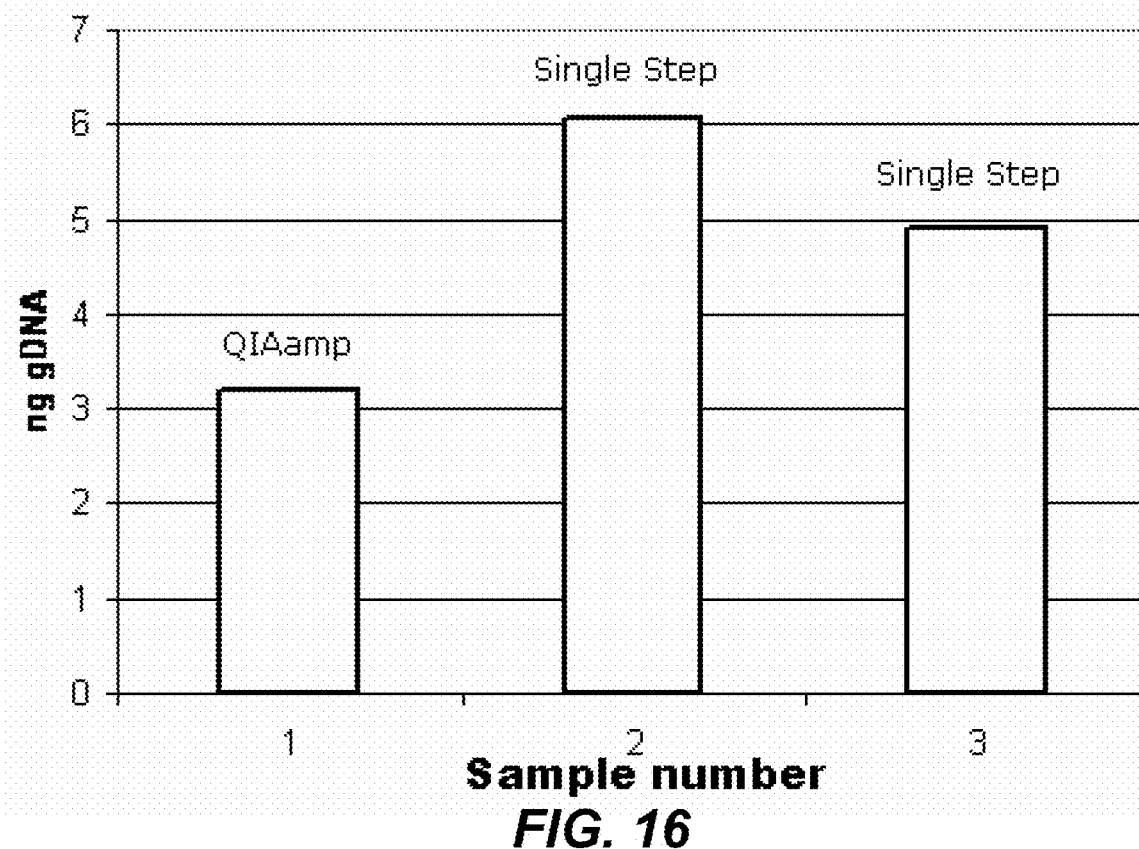
FIG. 16 shows the amount of gDNA obtained from FFPE rat liver tissue (Example 12) using a commercially available kit (1) and the method and device of the present invention (2 and 3).

To evaluate the amount and quality of the gDNA obtained, a SYBR Green-based RT-PCR was carried out on a TaqMan system using the gene coding for 18S rRNA as a target. The results are presented in FIGS. 15 and 16. While the CT-values obtained in the RT-PCR are comparable for both methods (the samples purified by the present invention having a slightly lower CT-value), the amount of gDNA obtained by using the device and the method of the present invention is about 1.5-fold to about almost twice as high as the amount of gDNA obtained by using the kit commercially available. As can be seen from FIG. 16, extending the lysis time to 1 h has an advantageous effect on the yield of gDNA obtained from FFPE samples.

The invention claimed is:

1. A method for purifying genomic deoxyribonucleic acid (DNA) by gel filtration chromatography, comprising:
    (a) mixing a biological sample comprising DNA including genomic DNA, ribonucleic acid (RNA) and proteins with a lysis buffer comprising a source of an anionic surfactant, and
    (b) selectively precipitating the anionic surfactant from the mixture of step (a) by adding to the mixture of step (a) a monovalent ion of an alkali metal and/or a divalent ion of an alkaline earth metal, thereby generating a mixture comprising the precipitated anionic surfactant,
    (c) establishing a solid matrix in a chromatographic unit, wherein the chromatographic unit comprises:
        (i) a hollow body having an inlet and an outlet and comprising the solid matrix, and
        (ii) a porous frit, filter, fleece or membrane placed between the outlet and the solid matrix to retain the solid matrix within the chromatographic unit,
        wherein the solid matrix is a gel-forming polymer having a size exclusion limit of 150 to 500 bp, and
    (d) applying the mixture of step (b) that comprises the precipitated anionic surfactant to an upper surface of the solid matrix, and
    (e) eluting the genomic DNA from the chromatographic unit as an eluate and simultaneously collecting the eluate.

2. The method of claim 1, wherein the chromatographic unit is a spin column, and wherein step (c) is performed by centrifugation (pre-spinning).

3. The method of claim 2, wherein the step of pre-spinning is carried out by centrifuging the chromatographic unit at 500 to 900×g for 1 to 7 min.

4. The method of claim 2, wherein the step of pre-spinning is carried out by centrifuging the chromatographic unit at 700×g for 2 to 5 min.

5. The method of claim 2, where the step of pre-spinning is carried out by centrifuging the chromatographic unit at 700×g for 3 min.

6. The method of claim 1, wherein the solid matrix is a gel-forming polymer having a size exclusion limit of 200 to 400 bp.

7. The method of claim 1, wherein the solid matrix is a gel-forming polymer having a size exclusion limit of 250 to 300 bp.

8. The method of claim 1, wherein the biological sample is a cell-containing biological sample selected from the group consisting of fresh and frozen tissue, body liquids, and Gram-negative bacteria.

9. The method of claim 1, wherein the biological sample is blood.

10. The method of claim 1, wherein the volume of matrix bed per chromatographic unit is in the range of 100 µL to 2 mL.

11. The method of claim 1, wherein the volume of matrix bed per chromatographic unit is in the range of 500 µL to 1 mL.

12. The method of claim 1, wherein the volume of matrix bed per chromatographic unit is 800 µL.

13. The method of claim 1, wherein a sample volume per 600 µL to 800 µl matrix bed is in the range of 10 to 100 µL.

14. The method of claim 1, wherein step (e) is carried out by centrifuging the chromatographic unit at 500 to 900×g for 1 to 7 min.

15. The method of claim 1, wherein step (e) is carried out by centrifuging the chromatographic unit at 700×g for 2 to 5 min.

16. The method of claim 1, wherein step (e) is carried out by centrifuging the chromatographic unit at 700×g for 3 min.

17. The method of claim 1, wherein the lysis procedure further comprises the step of disintegrating the RNA contained in the lysate.

18. The method of claim 1, wherein the monovalent ion of the alkali metal and/or the divalent ion of the alkaline earth metal comprise $Rb^+$, $Cs^+$, $Ca^{2+}$, $Sr^{2+}$, $Ba^{2+}$, or any mixture thereof.

19. The method of claim 1, wherein the source of the anionic surfactant is sodium dodecyl sulphate (SDS), ammonium dodecyl sulphate, lithium dodecyl sulphate, alkyl sulphate, alkane sulfonate, alkylbenzene sulfonate, or alkyl carboxylate.

20. The method of claim 1, wherein the chromatographic unit comprises a non-porous ring between the matrix and the porous fit, filter, fleece, or membrane, thereby sealing the outer area of the frit, filter, fleece or membrane.

21. The method of claim 1, further comprising performing PCR using the genomic DNA in the eluate directly as the template.

\* \* \* \* \*

UNITED STATES PATENT AND TRADEMARK OFFICE
CERTIFICATE OF CORRECTION

| | |
|---|---|
| PATENT NO. | : 11,253,797 B2 |
| APPLICATION NO. | : 15/204706 |
| DATED | : February 22, 2022 |
| INVENTOR(S) | : Roland Fabis et al. |

It is certified that error appears in the above-identified patent and that said Letters Patent is hereby corrected as shown below:

In the Claims

<u>Column 25, Claim 20, Line 20:</u>
"porous fit, filter, fleece," should read: --porous frit, filter, fleece,--.

Signed and Sealed this
Nineteenth Day of September, 2023

Katherine Kelly Vidal
*Director of the United States Patent and Trademark Office*